US009371346B2

(12) United States Patent
Ostermaier

(10) Patent No.: US 9,371,346 B2
(45) Date of Patent: Jun. 21, 2016

(54) PREPARING A NICKEL PHOSPHORUS LIGAND COMPLEX

(75) Inventor: John J. Ostermaier, Orange, TX (US)

(73) Assignee: INVISTA North America S.a.r.l., Wilmington, DE (US)

(*) Notice: Subject to any disclaimer, the term of this patent is extended or adjusted under 35 U.S.C. 154(b) by 76 days.

(21) Appl. No.: 13/821,162

(22) PCT Filed: Jun. 13, 2011

(86) PCT No.: PCT/US2011/040193
§ 371 (c)(1),
(2), (4) Date: May 10, 2013

(87) PCT Pub. No.: WO2012/033556
PCT Pub. Date: Mar. 15, 2012

(65) Prior Publication Data
US 2013/0345459 A1 Dec. 26, 2013

Related U.S. Application Data

(60) Provisional application No. 61/380,445, filed on Sep. 7, 2010.

(30) Foreign Application Priority Data

Dec. 15, 2010 (WO) ................ PCT/US2010/060381

(51) Int. Cl.
C07F 15/04 (2006.01)
C22B 23/02 (2006.01)
B01J 31/22 (2006.01)
B01J 31/18 (2006.01)
C07F 19/00 (2006.01)

(52) U.S. Cl.
CPC ............. *C07F 15/04* (2013.01); *B01J 31/1845* (2013.01); *C07F 15/045* (2013.01); *C22B 23/02* (2013.01); *C22B 23/021* (2013.01); *B01J 31/185* (2013.01); *B01J 31/22* (2013.01); *B01J 2231/322* (2013.01); *B01J 2531/847* (2013.01); *C07F 19/005* (2013.01)

(58) Field of Classification Search
CPC .... C22B 23/02; C22B 23/021; B01J 31/1845; B01J 31/185; B01J 31/22; B01J 2231/322; B01J 2531/847; C07F 19/005
USPC .......................................................... 556/13
See application file for complete search history.

(56) References Cited

U.S. PATENT DOCUMENTS

| 2,913,348 | A | 11/1959 | Jackson et al. |
|---|---|---|---|
| 3,350,167 | A | 10/1967 | Mcmullen et al. |
| 3,399,050 | A | 8/1968 | Evans et al. |
| 3,496,215 | A | 2/1970 | Drinkard et al. |
| 3,496,217 | A | 2/1970 | Drinkard et al. |
| 3,631,191 | A | 12/1971 | Kane et al. |
| 3,655,723 | A | 4/1972 | Drinkard et al. |
| 3,672,873 | A | 6/1972 | Huggins et al. |
| 3,766,237 | A | 10/1973 | Chia et al. |
| 3,816,098 | A | 6/1974 | Mackiw et al. |
| 3,846,461 | A | 11/1974 | Shook, Jr. |
| 3,847,959 | A | 11/1974 | Shook, Jr. et al. |
| 3,903,120 | A | 9/1975 | Shook, Jr. et al. |
| 3,914,124 | A | 10/1975 | O'Neill et al. |
| 4,045,541 | A | 8/1977 | Mercer |
| 4,118,342 | A | 10/1978 | Debus et al. |
| 4,416,825 | A | 11/1983 | Ostermaier |
| 4,591,579 | A | 5/1986 | Lok et al. |
| 4,670,416 | A | 6/1987 | Klimmek et al. |
| 4,749,801 | A | 6/1988 | Beatty et al. |
| 4,946,068 | A | 8/1990 | Erickson et al. |
| 5,087,599 | A | 2/1992 | Botman et al. |
| 5,512,696 | A | 4/1996 | Kreutzer et al. |
| 5,523,453 | A * | 6/1996 | Breikss .......................... 558/338 |
| 5,688,986 | A | 11/1997 | Tam et al. |
| 5,723,641 | A | 3/1998 | Tam et al. |
| 5,787,353 | A | 7/1998 | Kibbe et al. |
| 5,981,722 | A | 11/1999 | Chen et al. |
| 6,069,267 | A | 5/2000 | Tam |
| 6,127,567 | A * | 10/2000 | Garner et al. ................. 558/338 |

(Continued)

FOREIGN PATENT DOCUMENTS

| CH | 127157 A | 8/1928 |
|---|---|---|
| CN | 1765549 A | 5/2006 |

(Continued)

OTHER PUBLICATIONS

Vasserman et al., "Separation of Substances from Solutions by Chemical Precipitation. I. Chemical Aging of Basic Nickel Carbonate Precipitates and the Mechanism of Sodium Carbonate Utilization in the Process of Precipitation", Zhurnal Prikladnoi Khimii (Sankt-Peterburg, Russian Federation), 31, CODEN: ZPKHAB, ISSN: 0044-4618, Copyright: 2010 ACS on STN, 1958, pp. 1617-1624.

Xiang et al., "Experimental Study on Synthesis of Nio Nano-Particles", Scripta Materialia, 47(4), CODEN: SCMAF7, ISSN: 1359-6462, Department of Chemical Engineering, Tsinghua University, Beijing, 100084, Peop. Rep. China, Copyright: 2010 ACS on STN, 2002, pp. 219-224.

Xueyi et al., "Study on the Thermodynamic Equilibrium of the Complex System of Ni(li)—Nh3—Co32—H2o and Its Application to the Precipitation of Basic Nickel Carbonate Particles", EPD Congress 2004 as held at the 2004 TMS Annual Meeting (2004), Photomicrographs, Numerical Data, Graphs, 7 reference Published by: Minerals, Metals and Materials Society (TMS). 184 Thorn Hill Road, Warrendale, PA 15086-7528, USA Conference: EPD Congress 2004 as held at the TMS Annual Meeting, Charlotte, NC, USA, ISBN: 0-87339-565-4, Central-South University of Changsha, Hunan, 410083, P. R. China.

(Continued)

Primary Examiner — Jafar Parsa
Assistant Examiner — Medhanit Bahta
(74) Attorney, Agent, or Firm — Robert B. Furr, Jr.; Nicholas P. Lanzatella

(57) ABSTRACT

The present invention relates to a method of preparing a nickel complex including nickel and at least one phosphorus-containing ligand by reacting at least a portion of a nickel metal with at least one phosphorus-containing ligand. The nickel metal is prepared from a nickel composition including nickel(II).

23 Claims, No Drawings

(56) References Cited

U.S. PATENT DOCUMENTS

| | | | |
|---|---|---|---|
| 6,171,996 B1 | 1/2001 | Garner et al. | |
| 6,242,633 B1* | 6/2001 | Fischer et al. | 558/334 |
| 6,494,931 B1 | 12/2002 | Mukuno et al. | |
| 6,524,994 B1 | 2/2003 | Reesink et al. | |
| 6,592,645 B1* | 7/2003 | Mizutani et al. | 75/365 |
| 6,906,218 B2 | 6/2005 | Allgeier et al. | |
| 7,056,565 B1 | 6/2006 | Cai et al. | |
| 7,345,006 B2 | 3/2008 | Bartsch et al. | |
| 7,470,805 B2 | 12/2008 | Rosier et al. | |
| 7,528,275 B2 | 5/2009 | Bartsch et al. | |
| 7,531,682 B2 | 5/2009 | Galland et al. | |
| 7,629,484 B2 | 12/2009 | Ritter | |
| 7,659,422 B2* | 2/2010 | Foo et al. | 558/338 |
| 7,709,674 B2* | 5/2010 | Foo et al. | 558/332 |
| 7,854,973 B2 | 12/2010 | Dey | |
| 7,919,646 B2* | 4/2011 | Garner et al. | 558/338 |
| 8,815,186 B2 | 8/2014 | Ostermaier | |
| 8,969,606 B2 | 3/2015 | Medhekar et al. | |
| 9,050,591 B2 | 6/2015 | Fraga-Dubreuil et al. | |
| 2003/0100442 A1 | 5/2003 | Chu et al. | |
| 2003/0100802 A1 | 5/2003 | Shapiro | |
| 2003/0144440 A1 | 7/2003 | Gagne et al. | |
| 2004/0106815 A1 | 6/2004 | Ritter | |
| 2006/0107792 A1 | 5/2006 | Collins et al. | |
| 2008/0015381 A1 | 1/2008 | Foo et al. | |
| 2011/0196168 A1 | 8/2011 | Ostermaier | |
| 2011/0311428 A1 | 12/2011 | Ostermaier | |
| 2013/0143730 A1 | 6/2013 | Fraga-Dubreuil et al. | |
| 2013/0144079 A1 | 6/2013 | Medhekar et al. | |
| 2013/0144082 A1 | 6/2013 | Fraga-Dubreuil et al. | |
| 2013/0317242 A1 | 11/2013 | Ostermaier | |

FOREIGN PATENT DOCUMENTS

| | | |
|---|---|---|
| CN | 101016173 A | 8/2007 |
| CN | 101478044 A | 7/2009 |
| CN | 101519229 A | 9/2009 |
| CN | 101708868 A | 5/2010 |
| CN | 101733106 A | 6/2010 |
| EP | 114704 A2 | 8/1984 |
| EP | 0354612 B1 | 12/1991 |
| EP | 496448 B1 | 3/1994 |
| EP | 673841 A2 | 9/1995 |
| EP | 985448 A1 | 3/2000 |
| EP | 1724363 A1 | 11/2006 |
| FI | 115522 B | 5/2005 |
| FR | 1400059 A | 5/1965 |
| GB | 146407 A | 11/1921 |
| GB | 255884 A | 4/1927 |
| GB | 703826 A | 2/1954 |
| GB | 1437191 A | 5/1976 |
| GB | 1437192 A | 5/1976 |
| GB | 2465467 A | 5/2010 |
| JP | 5896802 A | 6/1983 |
| JP | 61106422 A | 5/1986 |
| JP | 1153534 A | 6/1989 |
| JP | 2172829 A | 7/1990 |
| JP | 03-249943 A | 11/1991 |
| JP | 07-005494 A | 1/1995 |
| JP | 2001335326 A | 12/2001 |
| RU | 2102137 C1 | 1/1998 |
| SU | 116020 A1 | 11/1958 |
| SU | 254781 A | 10/1969 |
| SU | 710958 A1 | 1/1980 |
| WO | 2006052677 A1 | 5/2006 |
| WO | 2007/130206 A9 | 6/2008 |
| WO | 2010/088863 A1 | 8/2010 |
| WO | 2011075494 A1 | 6/2011 |
| WO | 2011075496 A1 | 6/2011 |
| WO | 2011094411 A1 | 8/2011 |
| WO | 2012/033556 A1 | 3/2012 |
| WO | 2012170297 A2 | 12/2012 |
| WO | 2012170300 A2 | 12/2012 |
| WO | 2012170537 A2 | 12/2012 |

OTHER PUBLICATIONS

Zhou et al., "Study of Removal of Heavy Metals from Industrial Wastewater", Zhongguo Jishui Paishui, 14(4), CODEN: ZGPAFP; ISSN: 1000-4602, Nanjing University, Nanjing, Peop. Rep. China, Copyright: 2010 ACS on STN, 1998, pp. 17-20.

Cloutier et al., "The Study of the Precipitation of Carbonates", Proceedings and Transactions of the Royal Society of Canada , 33(III), CODEN: PTRCBI; ISSN: 0316-4616,2010 ACS on STN, 1936, pp. 149-164.

Lascelles et al., "Nickel Compounds", In: Ullman's Encyclopedia of Industrial Chemistry, vol. 24, Wiley-VCH Verlag GmbH & Co., Weinheim, Germany, 2005, pp. 117-131.

Liu et al., "An Improved Purification Method for Preparation of Basic Nickel Carbonate of High Purity Via Chemical Precipitation", Journal of Wuhan University of Technology (Materials Science Edition) (Jun. 2008) 23, (3), Published by: Wuhan University of Technology, 122 Luoshi Road, Wuhan, 430070, China, mailto: jwtu@mail.whut.edu.cn, URL: whjtkjdxxb.periodicals.net.cn ISSN: 1000-2413, College of Chemical Engineering, Sichuan University, Chengdu, 610065, China, Copyright: 2010 CSA on STN, 2008, pp. 331-333.

Richardson et al., "In Situ Generation of Ni Metal Nanoparticles as Catalyst for H2-Rich Syngas Production from Biomass Gasification", Applied Catalysis A: General, 382(2), 2010, pp. 220-230.

International Preliminary Report on Patentability received for PCT Patent Application No. PCT/US2012/041107, mailed on Oct. 17, 2013, 28 pages.

International Search Report received for PCT Patent Application No. PCT/US2012/041107, mailed on Mar. 15, 2013, 7 pages.

Written Opinion received for PCT Patent Application No. PCT/US2012/041107, mailed on Mar. 15, 2013, 14 pages.

"Sodium carbonate—SIDS Initial Assessment Report for SIAM 15", UNEP Publications, Feb. 19, 2003.

Brunauer et al., "Adsorption of Gases in Multimolecular Layers", J. Am. Chem. Soc. 60, 1938, pp. 309-319.

Chen et al., "Resistivity to Sulfur Poisoning of Nickel-Alumina Catalysts", Ind. Eng. Chem. Res. 27(8), 1988, pp. 1391-1396.

Crosa et al., "Determination of Mean Crystalite Dimensions from X-Ray Diffraction Peak Profiles: A Comparative Analysis of Synthetic Hematites", Clays and Clay Materials, 47(6), 1999, pp. 742-747.

Formanek et al., "Iron, 3. Direct Reduction Processes", In: Ullmann's Encyclopedia of Industrial Chemistry. vol. 19, Wiley-VCH Verlag GmbH & Co., Weinheim, Germany, 2000, pp. 711-726.

Greenwood et al., "Nickel, Palladium and Platinum", In: Chemistry of the Elements (1st Edition), Pergamon Press, Oxford, 1984, pp. 1328-1363.

Kerfoot, Derek, "Nickel", In: Ullman's Encyclopedia of Industrial Chemistry, vol. 24, Wiley-VCH Verlag GmbH & Co., Weinheim, DE, 2000, pp. 37-101.

Taylor et al., "Synthesis and Crystal Structure of the Novel Cyclometallophosphine Complex Re4C12(CO)15-{MePP(Me)PMe}", Journal of the Chemical Society, Chemical Communications, 8, 1985, pp. 476-477.

Rhamdhani, et al., "Basic Nickel Carbonate Part I and Part II" In: Metallurgical and Materials Transactions B2008, vol. 39B, Apr. 2008, pp. 218-245.

Tolman et al., "Homogeneous Nickel-Catalyzed Olefin Hydrocyanation" Advances in Catalysis, 33, 1985, pp. 1-46.

Machine Translation of JP 2001-335326, Retrieved from <http://dossier.idpl.go.jp/text_trans.html> dated Mar. 11, 2013.

Carlsson et al., "Coprecipitation of Ni with CaCO3: an Experimental Study", Report, VIT-TIED-1712, VTT/RN-1712, ISBN-951-38-4866-3, Order No. PB96-187497GAR, Avail.: NTIS From: Gov. Rep. Announce. Index (U. S.), 96 (17), Abstract No. 17-01,973, Chemical Technology, Valtion Teknillinen Tutkimuskeskus, Espoo, Finland, Copyright: 2010 ACS on STN, 1995, 29 pages.

Carriel et al., "Composition of Basic Nickel Carbonates", Journal of the American Chemical Society, 76, CODEN: JACSAT, ISSN: 0002-7863, Mellon Inst., Pittsburgh, PA, Copyright: 2010 ACS on STN, 1954, pp. 3839-3843.

(56) References Cited

OTHER PUBLICATIONS

Costodes, Taty V.C, "Reactive Crystallization of Nickel Hydroxy-Carbonate in Fluidized-Bed Reactor: Fines Production and Column Design", Chemical Engineering Science, 61(5), CODEN: CESCAC, ISSN: 0009-2509, Precipitation and Crystallization Research Facility, Department of Chemical Engineering, University of Cape Town, Cape Town, S. Afr., Copyright: 2010 ACS on STN, 2006, pp. 1377-1385.

Davidson et al., "Nucleation Kinetics in the Reactions of Nickel Basic Carbonates with Hydrogen Sulfide: The Carbonate Precipitation Reactions of Divalent Nickel", Industrial & Engineering Chemistry Research, 46(14), CODEN: IECRED, ISSN: 0888-5885, School of Engineering and Electronics, University of Edinburgh, Edinburgh, EH9 3JL, UK, Copyright: 2010 ACS on STN, 2007, pp. 4772-4777.

Evlash et al., "Precipitation of Basic Nickel Carbonate", Zhurnal Prikladnoi Khimii (Sankt-Peterburg, Russian Federation), 58(11), CODEN: ZPKHAB, ISSN: 0044-4618, Copyright: 2010 ACS on STN, 1985, pp. 2417-2421.

Gagnon et al., "Contribution to the Study of the Precipitation of Carbonates, Borates, Silicates and Arsenates", Canadian Journal of Research, Section B: Chemical Sciences, 19, B, CODEN: CNRBAX; ISSN: 0366-7391, Copyright: 2010 ACS on STN, 1941, pp. 179-204.

Guillard et al., "Nickel Carbonate Precipitation in a Fluidized-ed Reactor", Industrial & Engineering Chemistry Research, 40(23), CODEN: IECRED, ISSN: 0888-5885, Precipitation and Crystallization Research Facility Chemical Engineering Department, University of Cape Town, Rondebosch, 7701, S. Afr., Copyright: 2010 ACS on STN, 2001, pp. 5564-5569.

Guillard et al., "Optimization of Nickel Hydroxycarbonate Precipitation Using a Laboratory Pellet Reactor", Industrial & Engineering Chemistry Research, 41(13), CODEN: IECRED, ISSN: 0888-5885, Precipitation and Crystallisation Research Facility, Chemical Engineering Department, University of Cape Town, Cape Town, 7701, S. Afr., Copyright: 2010 ACS on STN, 2002, pp. 3110-3114.

Guo et al., "Preparation of Basic Nickel Carbonate Particles in Solution System of Ni(II)—NH3—CO2—3—H2O", Transactions of the Nonferrous Metals Society of China (2004), vol. 14, (5), Numerical Data, Graphs, Photomicrographs, Spectra, 15 reference Published by: Nonferrous Metals Society of China, Central South University of Technology, School of Metallurgical Science and Engineering, Central South University, Changsha 410083, China, ISSN: 1003-6326, Copyright: 2010 CSA on STN, 2004, pp. 1006-1011.

Hoffmann et al., "Preliminary Results on the Behaviour of Ni(II) in the Calcite-Water System", Mineralogical Magazine, 62A(Pt. 2), CODEN: MNLMBB, ISSN: 0026-461X, Geological Institute, University of Copenhagen, Copenhagen, DK-1350, Den., Copyright: 2010 ACS on STN, 1998, pp. 642-643.

Jaulmes et al., "Solubility and Precipitation of Slightly Soluble Salts of Weak or Moderately Strong Acids", Travaux de la Societe de Pharmacie de Montpellier, 25(2), CODEN: TSPMA6, ISSN: 0037-9115, University Montpellier, Fr., Copyright: 2010 ACS on STN, 1965, pp. 98-110.

Kucha et al., "Manufacture of Basic Nickel Carbonate", Issled. i Razrab. Syr'ya dlya Prigot. Katalizatorov, M., From: Reference Zh., Khim., Abstract No. 12L142, Copyright: 2010 ACS on STN, 1991, pp. 41-43.

Lee et al., "A Study on Nickel Hydroxide Crystallization Characteristics", Korean Journal of Chemical Engineering 22(5), CODEN: KJCHE6, ISSN: 0256-1115, Dept. of Chemical Engineering, Kongju National University, Kongju, 314-701, S. Korea, Copyright: 2010 ACS on STN, 2005, pp. 712-716.

Lewis, A. E., "Fines Formation (and prevention) in Seeded Precipitation Processes", KONA, 24, CODEN: KONAE7, ISSN: 0288-4534, Crystallization and Precipitation Unit, Department of Chemical Engineering, University of Cape Town, Cape Town, 7701, South Africa, Copyright: 2010 ACS on STN, 2006, pp. 119-125.

Li et al., "Formation of Dispersive NiO Nano-particles via Hydrothermal Modification", Xiyou Jinshu Cailiao yu Gongcheng (Rare Metal Materials and Engineering), 33, (4), Graphs, Spectra, Photomicrographs, 13 reference, Published by: Northwest Institute for Non-Ferrous Metal Research, Editorial Office of Rare Metal Materials and Engineering, Xi'an Shaanxi, 710016, China ISSN: 1002-185X, Tsinghua University (China), Copyright: 2010 CSA on STN, Apr. 2004, pp. 425-428.

Ueno et al., "Influence of the Conditions of Precipitation on the Activity of Nickel Catalysts. II. Precipitation with Sodium Carbonate", Kogyo Kagaku Zasshi, 46, CODEN: KGKZA7, ISSN: 0368-5462, Copyright: 2010 ACS on STN, 1943, pp. 45-47.

Makarov et al., "Optimization of Natural Water Purification to Remove Nickel and Copperions With Carbonate Flour", Russian Journal of Applied Chemistry (Translation of Zhurnal Prikladnoi Khimii), 74(12), CODEN: RJACEO, ISSN: 1070-4272, Tananaev Institute of Chemistry and Technology of Rare Elements and Mineral Raw Materials, Kola Scientific Center, Russian Academy of Sciences, Apatity, Russia, Copyright: 2010 ACS on STN, 2001, pp. 2045-2050.

Mallya et al., "Basic Nickel Carbonates. I. Factors which Influence the Precipitation of Nickel Carbonates", Journal of the Indian Institute of Science, 43, CODEN: JIISAD; ISSN: 0019-4964, Indian Inst. Sci., Bangalore, Copyright: 2010 ACS on STN, 1961, pp. 44-51.

Mallya et al., "Basic Nickel Carbonates. II. Hydration of Basic Nickel Carbonate", Journal of the Indian Institute of Science, 43, CODEN: JIISAD, ISSN: 0019-4964, Indian Inst. Sci., Bangalore, Copyright: 2010 ACS on STN, 1961, pp. 65-75.

Mallya et al., "Basic Nickel Carbonates. III. Potentiometric Investigation of the Precipitation", Journal of the Indian Institute of Science, 43, CODEN: JIISAD; ISSN: 0019-4964, Indian Inst. Sci., Bangalore, Copyright: 2010 ACS on STN, 1961, pp. 76-86.

Mallya et al., "Basic Nickel Carbonates. IV. Preparation of Basic Nickel Carbonate and Its Differential Thermal Analysis", Journal of the Indian Institute of Science, 43, From: CZ 1962(34), 12221-2. CODEN: JIISAD; ISSN: 0019-4964, Indian Inst. Sci., Bangalore, Copyright: 2010 ACS on STN, 1961, pp. 87-96.

Mallya et al., "Basic Nickel Carbonates. V. Thermogravimetric Behavior of Basic Nickel Carbonates", Journal of the Indian Institute of Science, 43(3), CODEN: JIISAD, ISSN: 0019-4964, Indian Inst. Sci., Bangalore, Copyright: 2010 ACS on STN, 1961, pp. 131-140.

Mallya et al., "Basic Nickel Carbonates. VI. Thermal Decomposition of Basic Nickel Carbonates in Vacuum and the Nature of the Surfaces", Journal of the Indian Institute of Science, 43(3), CODEN: JIISAD; ISSN: 0019-4964, Indian Inst. Sci., Bangalore, Copyright: 2010 ACS on STN, 1961, pp. 141-147.

Mallya et al., "Basic Nickel Carbonates. VII. Formation and Configurations of Basic Nickel Carbonates", Journal of the Indian Institute of Science, 43(3), From: CZ 1964(49), Abstract No. 0597-9. CODEN: JIISAD; ISSN: 0019-4964, Indian Inst. Sci., Bangalore, Copyright: 2010 ACS on STN, 1961, pp. 148-157.

Minkova et al., "Precipitation Processes in Obtaining Nickel(II) Hydroxocarbonate and Co-Precipitation of Other Nickel Hydroxo Salts. II. Influence of the Conditions for Obtaining Nickel(II) Hydroxocarbonate on the Amount of Co-Precipitated Sulfate Ions", Izvestiya po Khimiya, 16(4), 432-5 CODEN: IZKHDX, ISSN: 0324-0401, Inorg. Salts Res. Laboratory, Sofia, 1040, Bulg., Copyright: 2010 ACS on STN, 1983, pp. 432-435.

Minkova et al., "Precipitation Processes in Obtaining Basic Nickel(II) Carbonate and Coprecipitation of Other Basic Nickel Salts. I. Preparation of Basic Nickel Carbonate Free of Sulfate Ions", Izvestiya po Khimiya, 13(2), CODEN: IZKHDX, ISSN: 0324-0401, Chemical Reagents Prepare Laboratory, Sofia, 1040, Bulg., Copyright: 2010 ACS on STN, 1980, pp. 222-228.

Nassler, J., "A New Type of Basic Nickel(II) Carbonate", Collection of Czechoslovak Chemical Communications 29(1), CODEN: CCCCAK, ISSN: 0010-0765, Karlova University, Prague, Copyright: 2010 ACS on STN, 1964, pp. 168-173.

Noguchi et al., "Research on Recovery of Valuable Metal from Plating Waste Water—(1) Recovery of Nickel by Compound Precipitation Method", Journal of the Mining and Materials Processing Institute of Japan vol. 120, (4-5), Graphs, Numerical Data, Photomicrographs, Spectra, 16 reference, Kyushu University of Technology, Copyright: 2010 CSA on STN, 2004, pp. 209-216.

(56) References Cited

OTHER PUBLICATIONS

Ozheredova et al., "Nickel-Containing Rinsing Waters. Effect of Additives and the Nature of the Precipitant on the Degree of Treatment", Khimichna Promislovist Ukraini (Kiev, Ukraine), (3), CODEN: KPUKB8, Vostochnoukr. Nats. University im. V. Dalya, Ukraine, Copyright: 2010 ACS on STN, 2005, pp. 41-43.
Pistorius, C.W.F.T, "High Pressure Preparation and Structure of Crystalline Nickelous Carbonate", Experientia 15, CODEN: EXPEAM; ISSN: 0014-4754, University of California, Los Angeles, Copyright: 2010 ACS on STN, 1959, pp. 328-329.
Rossetti-Francois et al., "Structure and Constitution of Basic Nickel Carbonates", Journal de Chimie Physique et de Physico-Chimie Biologique, 51, CODEN: JCPBAN; ISSN: 0021-7689, Sorbonne, Paris, Copyright: 2010 ACS on STN, 1954, pp. 451-460.
Sergeev, M., "The Influence of Temperature on the Precipitation of Nickel Carbonate", Masloboino-Zhirovoe Delo, (No. 11), 15 CODEN: MZHDAD; ISSN: 0369-304X, Copyright: 2010 ACS on STN, 1928.
Packter et al., "Precipitation of Basic Nickel Carbonate Powders from Aqueous Solution. Crystallite Numbers, Composition, and Final Sizes", Kristall und Technik 10(9), CODEN: KRTEAW; ISSN: 0023-4753, Chemical Dep., North-East London Polytech., London, UK, Copyright: 2010 ACS on STN, 1975, pp. 985-994.
Van Weert et al., "The Production of Nickel Carbonate Spheroids From Dilute Solutions in a Pellet Reactor", Published by: The Minerals, Metals & Materials Society. 420 Commonwealth Dr., Warrendale, Pennsylvania 15086, USA Conference: Extractive Metallurgy of Copper, Nickel and Cobalt. vol. I: Fundamental Aspects, Denver, Colorado, USA, Delft University of Technology, DHV Water, Copyright: 2010 CSA on STN, Feb. 21-25, 1993, pp. 1133-1144.
Vasserman et al., "Continuous Method for the Precipitation of Basic Nickel Carbonate by an Automated Process", Tsvetnye Metally (Moscow, Russian Federation), 37(12), CODEN: TVMTAX; ISSN: 0372-2929, Copyright: 2010 ACS on STN, 1964, pp. 25-31.
Vasserman et al., "Separation of Substances from Solutions by Chemical Precipitation. III. Automatic Control of the Process of Precipitation of Basic Nickel Carbonate in the System Ni (NO3)2—Na2CO3—H2O by the pH of the Solution", Kh. Z. Branina. Zhur. Priklad. Khim., 32, Copyright: 2010 ACS on STN, 1959, pp. 2619-2624.
Response filed for PCT Patent Application No. PCT/US2012/041107, on Jun. 17, 2013, to Written Opinion mailed on Mar. 15, 2013, 9 pages.
Non-Final Office Action received for U.S. Appl. No. 10/993,622, mailed on Jul. 8, 2009, 7 pages.
Ex-Parte Quale Action received for U.S. Appl. No. 12/968,341, mailed on Aug. 26, 2015, 4 pages.
Final Office Action received for U.S. Appl. No. 12/968,341, mailed on Nov. 6, 2013, 12 pages.
Non-Final Office Action received for U.S. Appl. No. 12/968,341, mailed on Feb. 12, 2015, 14 pages.
Non-Final Office Action received for U.S. Appl. No. 12/968,341, mailed on Mar. 20, 2013, 12 pages.
Notice of Allowance received for U.S. Appl. No. 12/968,341, mailed on Dec. 18, 2015, 7 pages.
Requirement for Restriction/Election Action received for U.S. Appl. No. 12/968,341, mailed on Aug. 28, 2012, 8 pages.
Response filed for U.S. Appl. No. 12/968,341 on Jan. 13, 2014 to Final Office Action mailed on Nov. 6, 2013, 15 pages.
Response filed for U.S. Appl. No. 12/968,341 on Jul. 11, 2013, to Non-Final Office Action mailed on Mar. 20, 2013, 20 pages.
Response filed for U.S. Appl. No. 12/968,341 on May 5, 2015, to Non-Final Office Action mailed on Feb. 12, 2015, 14 pages.
Response filed for U.S. Appl. No. 12/968,341 on Nov. 24, 2015 to Ex-Parte Quale Action mailed on Aug. 26, 2015, 11 pages.
Response filed for U.S. Appl. No. 12/968,341 on Oct. 22, 2012, to Requirement for Restriction/Election Action mailed on Aug. 28, 2012, 15 pages.
Final Office Action received for U.S. Appl. No. 12/968,373, mailed on Dec. 17, 2012, 12 pages.
Non-Final Office Action received for U.S. Appl. No. 12/968,373, mailed on Oct. 21, 2013, 12 pages.
Notice of Allowance received for U.S. Appl. No. 12/968,373, mailed on Apr. 25, 2014, 7 pages.
Response filed for U.S. Appl. No. 12/968,373 on Dec. 5, 2013 to Non-Final Office Action mailed on Oct. 21, 2013, 15 pages.
Response filed for U.S. Appl. No. 12/968,373 on Feb. 11, 2013 to Final Office Action mailed on Dec. 17, 2012, 11 pages.
Final Office Action received for U.S. Appl. No. 13/490,116, mailed on Apr. 16, 2014, 6 pages.
Non-Final Office Action received for U.S. Appl. No. 13/490,116, mailed on Feb. 19, 2014, 7 pages.
Notice of Allowance received for U.S. Appl. No. 13/490,116, mailed on Jun. 23, 2014, 5 pages.
Notice of Allowance received for U.S. Appl. No. 13/490,116, mailed on Oct. 29, 2014, 7 pages.
Response filed for U.S. Appl. No. 13/490,116 on Apr. 9, 2014 to Final Office Action mailed on Feb. 19, 2014, 11 pages.
Response filed for U.S. Appl. No. 13/490,116 on Jun. 12, 2014 to Non-Final Office Action mailed on Apr. 16, 2014, 10 pages.
Non-Final Office Action received for U.S. Appl. No. 13/490,177, mailed on Jun. 24, 2014, 7 pages.
Notice of Allowance received for U.S. Appl. No. 13/490,177, mailed on Dec. 31, 2014, 7 pages.
Response filed for U.S. Appl. No. 13/490,177 on Apr. 28, 2014 to Restriction Requirement mailed on Feb. 28, 2014, 12 pages.
Response filed for U.S. Appl. No. 13/490,177 on Sep. 19, 2014 to Non-Final Office Action mailed on Jun. 24, 2014, 16 pages.
Restriction Requirement received for U.S. Appl. No. 13/490,177, mailed on Feb. 28, 2014, 6 pages.
Advisory Action received for U.S. Appl. No. 13/490,207, mailed on Jul. 28, 2014, 3 pages.
Final Office Action received for U.S. Appl. No. 13/490,207, mailed on Apr. 15, 2015, 9 pages.
Final Office Action received for U.S. Appl. No. 13/490,207, mailed on May 19, 2014, 10 pages.
Non-Final Office Action received for U.S. Appl. No. 13/490,207, mailed on Oct. 21, 2014, 10 pages.
Non-Final Office Action received for U.S. Appl. No. 13/490,207, mailed on Oct. 22, 2013, 11 pages.
Non-Final Office Action received for U.S. Appl. No. 13/490,207, mailed on Sep. 4, 2015, 9 pages.
Response filed for U.S. Appl. No. 13/490,207 on Aug. 12, 2013 to Requirement for Restriction/Election Action mailed on Jun. 14, 2013, 14 pages.
Response filed for U.S. Appl. No. 13/490,207 on Aug. 19, 2014 to Final Office Action mailed on May 19, 2014, and Advisory Action mailed on Jul. 28, 2014, 13 pages.
Response filed for U.S. Appl. No. 13/490,207 on Dec. 3, 2015 to Non-Final Office Action mailed on Sep. 4, 2015, 15 pages.
Response filed for U.S. Appl. No. 13/490,207 on Feb. 20, 2014 to Non-Final Office Action mailed on Oct. 22, 2013, 15 pages.
Response filed for U.S. Appl. No. 13/490,207 on Jul. 13, 2015 to Final Office Action mailed on Apr. 15, 2015, 14 pages.
Response filed for U.S. Appl. No. 13/490,207 on Jul. 21, 2014 to Final Office Action mailed on May 19, 2014, 13 pages.
Response filed for U.S. Appl. No. 13/490,207 on Mar. 18, 2015 to Non-Final Office Action mailed on Oct. 21, 2014, 13 pages.
Restriction Requirement received for U.S. Appl. No. 13/490,207, mailed on Jun. 14, 2013, 16 pages.
Amendment After Notice of Allowance (Rule 312) filed for U.S. Appl. No. 13/821,174 on Mar. 11, 2015, 4 pages.
Non-Final Office Action received for U.S. Appl. No. 13/821,174, mailed on Jun. 27, 2014, 5 pages.
Notice of Allowance received for U.S. Appl. No. 13/821,174, mailed on Dec. 19, 2014, 5 pages.
Response filed for U.S. Appl. No. 13/821,174 on Sep. 19, 2014 to Non-Final Office Action mailed on Jun. 27, 2014, 8 pages.
International Preliminary Report on Patentability received for PCT Patent Application No. PCT/US2011/040193, mailed on Mar. 21, 2013, 7 pages.

(56) References Cited

OTHER PUBLICATIONS

International Search Report and Written Opinion received for PCT Patent Application No. PCT/US2011/040193, mailed on Jan. 11, 2012, 8 pages.

International Preliminary Report on Patentability received for PCT Patent Application No. PCT/US2012/040466, mailed on Nov. 14, 2013, 20 pages.

International Search Report and Written Opinion received for PCT Patent Application No. PCT/US2012/040466, mailed on Mar. 11, 2013, 11 pages.

Borodina, "Dependence of the Activity of Nickel and Copper Carbonates on the Conditions of Precipitation", Trudy Vsesoyuz. Nauch.-Issledovatel. Inst. Zhirov, 1957, pp. 83-90.

Ito, et al., "Characterization of a Particple Size Distribution in a Ni—C Granular Thin Film by Grazing Incidence Small-angle x-ray Scattering", Journal of Physics: Conference Series, vol. 83, 2007, pp. 1-4.

Mittemeijer, et al., "The "state of the art" of the Diffraction Analysis of Crystallite Size and Strain", Zeitschrift fUr Kristalloqraphie—Crvstalline Materials, vol. 223, No. 9, 2008, pp. 552-560.

Nitta, et al., "Preparation Chemistry of Precipitated Ni—SI02 Catalysts for Enantioselective Hydrogenation", Journal of Catalysis, vol. 96, No. 2, 1985, pp. 429-438.

Nordhei, et al., "Nanophase Cobalt, Nickel and Zinc Ferrites: Synchrotron XAS Study on the Crystallite Size Dependence of Metal Distribution", Physical Chemistry Chemical Physics, vol. 10, 2008, pp. 1053-1066.

Queneauc, et al., "Part II—The Inco Pressure Carbonyl (IPC) Process", Journal of Metals, 1969, pp. 41-45.

Scardi, Paolo, "Chapter 13. Microstructural Properties: Lattice Defects and Domain Size Effects", Powder Diffraction : Theory and Practice, Department of Materials Engineering and Industrial Technologies, 2008, pp. 376-413.

Teixeira, et al., "Deactivation of Steam Reforming Catalysts by Sintering: Experiments and Simulation", Chemical Enaineering Science vol. 54, No. 15-16, 1999, pp. 3609-3618.

Ungar, et al., "Crystallite Size Distribution and Dislocation Structure Determined by Diffraction Profile Analysis: Princiiples and Practical Application to Cubic and Hexagonal Crystals", Journal of Applied Crystalloaraphy. vol. 34, No. 3, 2001, pp. 298-310.

Vasserman, et al., "A Continuous Method of Precipitating Basic Nickel Carbonate with Complex Automation of the Process", Soviet J Nonferrous Metals, No. 12, 1964, pp. 27-32.

\* cited by examiner

PREPARING A NICKEL PHOSPHORUS LIGAND COMPLEX

CROSS REFERENCE TO RELATED APPLICATIONS

This application is a U.S. National Stage Filing under 35 U.S.C. 371 from International Application No. PCT/US2011/040193, filed on 13 Jun. 2011, and published as WO/2012/033556 on 15 Mar. 2012, which application claims the benefit of the filing dates of U.S. Provisional Application No. 61/380,445 filed on Sep. 7, 2010, and PCT/US2010/060381 filed Dec. 15, 2010, each of which is specifically incorporated herein by reference in its entirety.

FIELD OF THE INVENTION

The invention includes the preparation of a nickel complex including nickel and at least one phosphorus-containing ligand by reacting a nickel metal with at least one phosphorus-containing ligand.

BACKGROUND OF THE INVENTION

Hydrocyanation catalyst systems, particularly pertaining to the hydrocyanation of ethylenically unsaturated compounds, are known in the art. For example, systems useful for the hydrocyanation of butadiene to form pentenenitrile (PN) and in the subsequent hydrocyanation of pentenenitrile to form adiponitrile (ADN) are known in the commercially important nylon synthesis field.

The hydrocyanation of ethylenically unsaturated compounds using transition metal complexes with monodentate phosphite ligands is documented in the prior art. See, for example, U.S. Pat. Nos. 3,496,215; 3,631,191; 3,655,723; and 3,766,237, and Tolman et al., *Advances in Catalysis*, 1985, 33, 1. The hydrocyanation of activated ethylenically unsaturated compounds, such as with conjugated ethylenically unsaturated compounds (e.g., 1,3-butadiene and styrene), and strained ethylenically unsaturated compounds (e.g., norbornene) proceeds without the use of a Lewis acid promoter, while hydrocyanation of unactivated ethylenically unsaturated compounds, such as 1-octene and 3-pentenenitrile (3PN), requires the use of a Lewis acid promoter. Recently, catalyst compositions and processes for the hydrocyanation of monoethylenically unsaturated compounds using zero-valent nickel and bidentate phosphite ligands in the presence of Lewis acid promoters have been described; for example in U.S. Pat. Nos. 5,512,696; 5,723,641; and 6,171,996.

U.S. Pat. No. 3,903,120 describes the preparation of zerovalent nickel complexes of the types $Ni(MZ_3)_4$ and $Ni(MZ_3)_2A$; wherein M is P, As or Sb; Z is R or OR, wherein R is an alkyl or aryl radical having up to 18 carbon atoms and can be the same or different, and at least one Z is OR; A is a monoolefinic compound having 2 to 20 carbon atoms; the R radicals of a given $MZ_3$ of $Ni(MZ_3)_2A$ preferably being so chosen that the ligand has a cone angle of at least 130°; are prepared by reacting elemental nickel with the monodentate $MZ_3$ ligand at a temperature in the range of 0° C.-150° C. in the presence of a halogen-containing derivative of the monodentate $MZ_3$ ligand as a catalyst. A more rapid reaction is realized by carrying out the preparation in an organonitrile solvent.

U.S. Pat. No. 4,416,825 also describes an improved, continuous process for the preparation of hydrocyanation catalysts including zerovalent nickel complexes with monodentate organophosphorus compounds (ligands) by controlling the temperature of the reaction relative to the amount of monodentate ligand and conducting the reaction in the presence of a chlorine ion and organic nitrile such as adiponitrile.

U.S. Pat. No. 6,171,996 describes zero-valent nickel complexes including bidentate phosphite ligands can be prepared or generated according to techniques well known in the art, as described, for example, in U.S. Pat. Nos. 3,496,217; 3,631,191; 3,846,461; 3,847,959; and 3,903,120. For example, divalent nickel compounds can be combined with a reducing agent, to serve as a source of zero-valent nickel in the reaction. Suitable divalent nickel compounds are said to include compounds of the formula $NiY_2$ where Y is halide, carboxylate, or acetylacetonate. Suitable reducing agents are said to include metal borohydrides, metal aluminum hydrides, metal alkyls, Zn, Fe, Al, Na, or $H_2$. Elemental nickel, preferably nickel powder, when combined with a halogenated catalyst, as described in U.S. Pat. No. 3,903,120, is also a suitable source of zero-valent nickel.

SUMMARY OF THE INVENTION

In various embodiments, the present invention provides a method of preparing a nickel complex including nickel and at least one phosphorus-containing ligand, including the steps of:

(a). charging a nickel metal and at least one phosphorus-containing ligand to a first reaction zone; and (b). within the first reaction zone of step (a), reacting at least a portion of the nickel metal with the at least one phosphorus-containing ligand to form a reaction mixture including the nickel complex including nickel and the at least one phosphorus-containing ligand;

wherein at least a portion of the nickel metal charged in step (a) is prepared by the additional steps including:

(i). providing a nickel composition, including nickel(II); and (ii). reducing at least a portion of the nickel composition of step (i) to form the nickel metal.

Various embodiments of the present invention have certain unexpected advantages. For example, the BNC nickel produced by some embodiments of the method of the present invention can be converted to Ni(0) that is particularly well-suited to conversion to forming complexes with phosphorus-containing ligands. For example, the Ni(0) that is generated by some embodiments of the method of the present invention can be flowable, can have lower carbon content, smaller particle size, or broader particle size distributions. In some embodiments, the method of making BNC nickel, of making Ni(0), or both, can be more efficient than commercially acquiring BNC or Ni(0), and can provide BNC or Ni(0) with superior properties to those available commercially, including for example novel properties. In certain embodiments, the nickel-ligand complex can be synthesized efficiently and with high yield, and can be a highly effective hydrocyanation catalyst. In some embodiments, the nickel-ligand complex is particularly well-suited to catalyzing the hydrocyanation of pentenenitriles to give ADN.

In some embodiments, the at least one phosphorus-containing ligand can be a bidentate phosphorus-containing ligand, or a monodentate phosphorus-containing ligand. Step (a) can optionally further include charging at least one Lewis acid to the first reaction zone. Step (a) can optionally further include charging at least one pentenenitrile solvent to the first reaction zone.

In one embodiment, the present invention provides a first method of preparing a nickel complex including nickel and at least one bidentate phosphorus-containing ligand, including the steps of:

(a). charging a nickel metal, at least one bidentate phosphorus-containing ligand, at least one Lewis acid to a first reaction zone; and (b). within the first reaction zone of step (a), reacting at least a portion of the nickel metal with at least one bidentate phosphorus-containing ligand to form a reaction mixture including a nickel complex including nickel and at least one bidentate phosphorus-containing ligand;

wherein at least a portion of the nickel metal in charging step (a) is prepared by the additional steps including:

(i). providing a nickel composition including nickel(II) and at least one anion selected from the group consisting of carbonate, bicarbonate, oxalate, a $C_1$ to $C_6$ carboxylate, hydroxide, and oxide; and (ii). reducing at least a portion of the nickel composition provided in step (i) to form the nickel metal.

The term "bidentate" is well known in the art and means the ligand molecule contains two phosphorus atoms, and both phosphorus atoms of the ligand can bond to a single nickel atom to form the nickel complex of step (b).

The at least one bidentate phosphorus-containing ligand charged to the first reaction zone of step (a) can be at least one bidentate phosphorus-containing ligand selected from the group consisting of a bidentate phosphite, a bidentate phosphonite, a bidentate phosphinite, a bidentate phosphine, and a mixed bidentate ligand; wherein the mixed bidentate ligand is selected from the group consisting of a phosphite-phosphonite, a phosphite-phosphinite, a phosphite-phosphine, a phosphonite-phosphinite, a phosphonite-phosphine, and a phosphinite-phosphine.

The at least one bidentate phosphorus-containing ligand charged to the first reaction zone of step (a) can be selected from members of the group consisting of Formula IIIa, Formula IIIb, Formula IIIc, or any combination of such members,

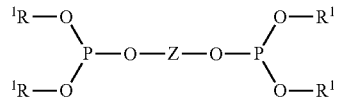

Formula IIIa

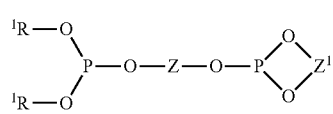

Formula IIIb

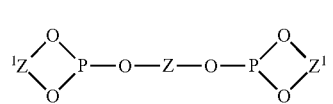

Formula IIIc wherein in Formulae IIIa, IIIb, and IIIc, $R^1$ is phenyl, unsubstituted or substituted with one or more $C_1$ to $C_{12}$ alkyl, $C_1$ to $C_{12}$ alkoxy groups, or groups of Formulae A and B, or $-(CH_2)_n OY^2$; or naphthyl, unsubstituted or substituted with one or more $C_1$ to $C_{12}$ alkyl or $C_1$ to $C_{12}$ alkoxy groups, or groups of Formulae A and B, or $-(CH_2)_n OY^2$; or 5,6,7,8-tetrahydro-1-naphthyl;

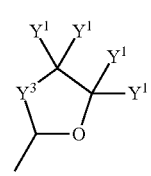

Formula A

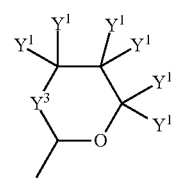

Formula B wherein in Formulae A and B, $Y^1$ is independently selected from the group of H, $C_1$ to $C_{18}$ alkyl, cycloalkyl, or aryl, $Y^2$ is independently selected from the group of $C_1$ to $C_{18}$ alkyl, cycloalkyl, or aryl, $Y^3$ is independently selected from the group of O or $CH_2$, and n=1 to 4; wherein in Formulae IIIa, IIIb, and IIIc, O—Z—O and O—$Z^1$—O are independently selected from the group consisting of structural Formulae IV, V, VI, VII, and VIII:

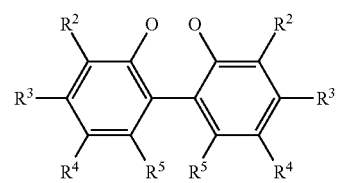

IV

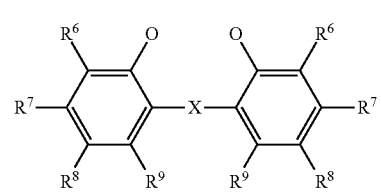

V wherein in Formulae IV and V, $R^2$, $R^3$, $R^4$, $R^5$, $R^6$, $R^7$, $R^8$, and $R^9$ are independently selected from the group consisting of H, $C_1$ to $C_{12}$ alkyl, and $C_1$ to $C_{12}$ alkoxy; X is O, S, or $CH(R^{10})$;

$R^{10}$ is H or $C_1$ to $C_{12}$ alkyl;

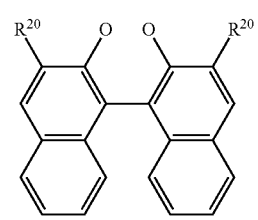

VI

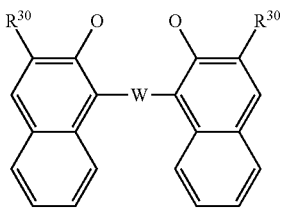

wherein in Formulae VI and VII, $R^{20}$ and $R^{30}$ are independently selected from the group consisting of H, $C_1$ to $C_{12}$ alkyl, and $C_1$ to $C_{12}$ alkoxy, and $CO_2R^{13}$;

$R^{13}$ is $C_1$ to $C_{12}$ alkyl or $C_6$ to $C_{10}$ aryl, unsubstituted or substituted with $C_1$ to $C_4$ alkyl;

W is O, S, or $CH(R^{14})$;

$R^{14}$ is H or $C_1$ to $C_{12}$ alkyl;

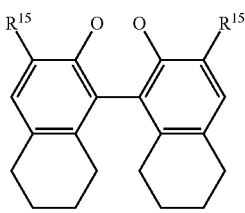

and wherein in Formulae VIII, $R^{15}$ is selected from the group consisting of H, $C_1$ to $C_{12}$ alkyl, and $C_1$ to $C_{12}$ alkoxy and $CO_2R^{16}$;

$R^{16}$ is $C_1$ to $C_{12}$ alkyl or $C_6$ to $C_{10}$ aryl, unsubstituted or substituted with $C_1$ to $C_4$ alkyl.

The first method can further include charging a pentenenitrile in step (a) wherein the pentenenitrile is selected from one or more members of the group consisting of 2-pentenenitrile, 3-pentenenitrile, 4-pentenenitrile, 2-methyl-3-butenenitrile, 2-methyl-2-butenenitrile. In one embodiment, the solvent includes between about 10% and about 100% by weight of 3-pentenenitrile.

To the first reaction zone of step (a), the first method can further include charging at least one monodentate phosphorus-containing ligand selected from the group consisting of a monodentate phosphite, a monodentate phosphonite, a monodentate phosphinite, and a monodentate phosphine.

The term "monodentate" is well known in the art and means each ligand molecule contains a single phosphorus atom that can bond to a single nickel atom, provided that the nickel atom can be complexed by one or more monodentate ligands to form the nickel complex of step (b).

The at least one Lewis acid charged to the first reaction zone of step (a) can be selected from the group consisting of inorganic or organometallic compounds that include an element selected from the group including scandium, titanium, vanadium, chromium, manganese, iron, cobalt, copper, zinc, boron, aluminum, yttrium, zirconium, niobium, molybdenum, cadmium, rhenium, lanthanum, europium, ytterbium, tantalum, samarium, and tin.

In one embodiment, the at least one Lewis acid is selected from the group consisting of zinc chloride, ferrous chloride, or a combination of zinc chloride and ferrous chloride.

The method can further include adjusting a first molar ratio between 0.5 and 2.5, wherein the first molar ratio is defined as total moles of the at least one Lewis acid charged in step (a) divided by total moles of the at least one bidentate phosphorus-containing ligand charged in step (a).

In one embodiment, the present invention provides a second method to prepare a nickel complex including nickel and at least one monodentate phosphorus-containing ligand, including the steps of:

(a). charging nickel metal and at least one monodentate phosphorus-containing ligand to a first reaction zone;

wherein the at least one monodentate phosphorus-containing ligand is selected from the group consisting of a monodentate phosphite, a monodentate phosphonite, a monodentate phosphinite, and a monodentate phosphine; and (b). within the first reaction zone of step (a), reacting at least a portion of the nickel metal with at least one monodentate phosphorus-containing ligand to form a reaction mixture including a nickel complex including nickel and at least one monodentate phosphorus-containing ligand;

wherein at least a portion of the nickel metal in charging step (a) is prepared by the additional steps including:

(i). providing a nickel composition including nickel(II) and at least one anion selected from the group consisting of carbonate, bicarbonate, oxalate, $C_1$ to $C_6$ carboxylate, hydroxide, and oxide; and (ii). reducing at least a portion of the nickel composition provided in step (i) to form the nickel metal.

Examples of the $C_1$ to $C_6$ carboxylates include carboxylates with a chemical formula of $HC(=O)O$, $H_3CC(=O)O$, $H_5C_2C(=O)O$, $H_7C_3C(=O)O$, $H_9C_4C(=O)O$, and $H_{11}C_5C(=O)O$.

The reducing of step (ii) can be performed with a reducing agent including carbonaceous material, hydrogen, or a combination of carbonaceous material and hydrogen. The temperature can be in a range of 150° C. to 700° C. and at a total pressure in a range of 0.01 atmosphere and 100 atmospheres. For example, the reducing of step (ii) of the first method can be performed with hydrogen as the reducing agent at a temperature between 200° C. to 600° C. for a period of time between 0.01 to 24 hours. For example, the reducing of step (ii) can be performed with a molar excess of hydrogen relative to the molar amount of nickel(II) in the nickel composition, at a total pressure in a range of 0.8 to 5 atmospheres, at a temperature between 250° C. to 350° C., and for a period of time between 0.16 to 12 hours to reduce greater than 90% of the nickel composition to the nickel metal.

A carbonaceous material can be, for example, a material including carbon, wherein the material can be oxidized. In one embodiment, the carbonaceous material can be selected from members of the group consisting of $C_1$ to $C_9$ hydrocarbons, natural gas, carbon monoxide, synthesis gas including carbon monoxide and hydrogen, fuel oil, coal, or any combination of such members.

The second method can further include charging to the first reaction zone in step (a) at least one halogenated catalyst including a phosphorus-halide bond selected from the group consisting of $PX_3$, $R^{17}PX_2$, $R^{18}OPX_2$, $[R^{19}][R^{20}]PX$, $[R^{21}][R^{22}O]PX$, and $[R^{23}O][R^{24}O]PX$; wherein $R^{17}$, $R^{18}$, $R^{19}$, $R^{20}$, $R^{21}$, $R^{22}$, $R^{23}$, and $R^{24}$ are independently selected from the group consisting of $C_1$ to $C_{18}$ hydrocarbyl radicals and each X is a halide independently selected from the group consisting of chloride, bromide, and iodide.

When at least one halogenated catalyst is charged to the first reaction zone in step (a), the second method can further include adjusting a second molar ratio between 5 and 1000, wherein the second molar ratio is defined as total moles of the halogenated catalyst charged in step (a) per million total moles of the at least one monodentate phosphorus-containing ligand charged in step (a).

In the second method, at least one Lewis acid can be charged to the first reaction zone of step (a) wherein the Lewis acid can be selected from the group consisting of inorganic or organometallic compounds in which the cation is selected from the group including scandium, titanium, vanadium, chromium, manganese, iron, cobalt, copper, zinc, boron, aluminum, yttrium, zirconium, niobium, molybdenum, cadmium, rhenium, lanthanum, europium, ytterbium, tantalum, samarium, and tin.

The method can further include charging an organonitrile in step (a), such as a pentenenitrile, selected from, for example, one or more members of the group consisting of 2-pentenenitrile, 3-pentenenitrile, 4-pentenenitrile, 2-methyl-3-butenenitrile, 2-methyl-2-butenenitrile, adiponitrile, 2-methylglutaronitrile, and ethylsuccinonitrile.

The nickel composition provided in step (i) can be selected from at least one nickel composition of the group consisting of a basic nickel(II) carbonate; nickel(II) hydroxide; nickel (II) oxide; hydrate complexes of basic nickel(II) carbonate, nickel(II) hydroxide, and nickel(II) oxide; and ammonia complexes of basic nickel(II) carbonate, nickel(II) hydroxide, and nickel(II) oxide. A basic nickel(II) carbonate can have a carbon to nickel mole ratio of equal to or less than 0.5, for example as measured by elemental analysis of a basic nickel (II) carbonate sample. For example, a carbon to nickel mole ratio from 0.01 to 0.5, for example, a carbon to nickel mole ratio from 0.2 to 0.5.

The basic nickel(II) carbonate provided in step (i) can be produced by precipitating the basic nickel(II) carbonate from at least one aqueous solution selected from the group consisting of (1) an aqueous solution including nickel(II), ammonia, ammonium carbonate, and water; (2) an aqueous solution including nickel(II), carbonate anions, and water; and (3) an aqueous solution including nickel(II), bicarbonate anions, and water.

The basic nickel(II) carbonate provided in step (i) can be produced from an ore including nickel. In another embodiment, the basic nickel(II) carbonate provided in step (i) of the first or second method can be produced from an ore including nickel and said basic nickel(II) carbonate can optionally include at least one element selected from the group consisting of aluminum, calcium, cobalt, copper, iron, magnesium, manganese, sodium, sulfur, and zinc.

The nickel composition provided in step (i) can be pre-heated between 150° C. to 700° C. prior to the reducing of step (ii). For example, the nickel composition provided in step (i) can be pre-heated between 200° C. to 600° C. The heating can take place in the presence of oxygen and/or inert gases like, for example, nitrogen, and other gases such as, for example, carbon dioxide, and steam. The heating can take place for a period of time between 0.01 to 24 hours prior to the reducing of additional step (ii).

Surface areas of the nickel metal from the reducing of additional step (ii) can fall within a range between about 0.5 to about 30 square meters per gram of nickel metal.

The reaction mixture temperature for the reacting step (b) can be adjusted between about 0° C. and about 150° C. In one example, the reaction mixture temperature can be adjusted between about 40° C. and about 100° C.

A nickel complex from the reaction mixture of step (b) can be contacted with 3-pentenenitrile and hydrogen cyanide in the presence of a Lewis acid promoter in a second reaction zone to produce adiponitrile.

A nickel complex from the reaction mixture of step (b) of the first or second method can also be contacted with 1,3-butadiene and hydrogen cyanide in a third reaction zone to produce 3-pentenenitrile, 2-methyl-3-butenenitrile, or a combination thereof.

A nickel complex from the reaction mixture of step (b) of the first or second method can be contacted with 2-methyl-3-butenenitrile in a fourth reaction zone to produce 3-pentenenitrile.

DETAILED DESCRIPTION OF THE INVENTION

The catalyst includes a zero-valent nickel and at least one phosphorus-containing (P-containing) ligand selected from the group consisting of a phosphite, a phosphonite, a phosphinite, a phosphine, and a mixed P-containing ligand or a combination of such members. As used herein, the term "mixed P-containing ligand" means a mixture of P-containing ligands including a combination of at least two multidentate P-containing ligands selected from the group consisting of a phosphite-phosphonite, a phosphite-phosphinite, a phosphite-phosphine, a phosphonite-phosphinite, a phosphonite-phosphine, and a phosphinite-phosphine.

The catalyst can include at least one monodentate P-containing ligand selected from the group consisting of a phosphite, a phosphonite, a phosphinite, and a phosphine or a combination of such members, provided that the monodentate P-containing ligand does not detract from the beneficial aspects of the invention. The monodentate P-containing ligand can be present as an impurity from the synthesis of the P-containing ligand, or the monodentate P-containing ligand can be added as a single or additional component of the catalyst. The monodentate P-containing ligand can be a mixture of P-containing ligands.

As used herein, the term "catalyst" includes within its meaning a catalyst precursor composition, indicating that the zero-valent nickel at some point becomes bound to at least one P-containing ligand, and further in all likelihood, additional reactions occur during hydrocyanation, such as, for example, complexing of the initial catalyst composition to an ethylenically unsaturated compound. As used herein, the term "catalyst" also includes within its meaning recycled catalyst, that is, a catalyst including a zero-valent nickel and at least one P-containing ligand which, having been used in the process of the invention, is returned or can be returned to the process and used again.

The term "hydrocarbyl" is well known in the art and designates a hydrocarbon molecule from which at least one hydrogen atom has been removed. Such molecules can contain single, double, or triple bonds.

The term "aryl" is well-known in the art and designates an aromatic hydrocarbon molecule from which at least one hydrogen atom has been removed. Examples of suitable aryl groups include, for example, those containing 6 to 10 carbon atoms, which can be unsubstituted or singly or multiply substituted. Suitable substituents include, for example, $C_1$ to $C_4$ hydrocarbyl, or halogen such as fluorine, chlorine, or bromine, or halogenated hydrocarbyl such as trifluoromethyl, or aryl such as phenyl.

The P-containing ligands chemically bonded to nickel as complexes, including zero-valent nickel, and the free P-containing ligands, not bonded to said complexes, can be monodentate or multidentate, for example bidentate or tridentate. The term "bidentate" is well known in the art and means that a single ligand molecule contains two phosphorus atoms, and both phosphorus atoms of the ligand are bonded to a single metal atom. The term "tridentate" means that a single ligand molecule contains three phosphorus atoms, and all three phosphorus atoms on the ligand are bonded to a single metal atom. The P-containing ligand can be a single compound or a mixture of compounds. The P-containing ligand can be selected from the group consisting of a phosphite, a phosphonite, a phosphinite, a phosphine, and a mixed P-containing ligand or a combination of such members. A multidentate P-containing ligand can be represented by Formula I.

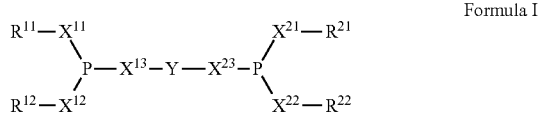

Formula I wherein, $X^{11}, X^{12}, X^{13}, X^{21}, X^{22}, X^{23}$ independently represent oxygen or a single bond;

$R^{11}, R^{12}$ independently represent identical or different, single or bridged organic radicals;

$R^{21}, R^{22}$ independently represent identical or different, single or bridged organic radicals; and Y represents a bridging group.

It is to be understood that Formula I can represent a single compound or a mixture of different compounds having the indicated formula.

In one embodiment, all of the groups $X^{11}, X^{12}, X^{13}, X^{21}, X^{22}, X^{23}$ can represent oxygen. In such a case, the bridging group Y is joined to phosphite groups. In such a case, the multidentate P-containing ligand represented by Formula I is a phosphite.

In another embodiment, $X^{11}$ and $X^{12}$ can each represent oxygen, and $X^{13}$, a single bond; or $X^{11}$ and $X^{13}$ can each represent oxygen and $X^{12}$, a single bond, so that the phosphorus atom surrounded by $X^{11}, X^{12}$, and $X^{13}$ is the central atom of a phosphonite. In such a case, $X^{21}, X^{22}$, and $X^{23}$ can each represent oxygen, so that the phosphorus atom surrounded by $X^{21}, X^{22}$, and $X^{23}$ can be the central atom of a phosphite; or $X^{21}$ and $X^{22}$ can each represent oxygen and $X^{23}$, a single bond; or $X^{21}$ and $X^{23}$ can each represent oxygen and $X^{22}$, a single bond, so that the phosphorus atom surrounded by $X^{21}, X^{22}$, and $X^{23}$ can be the central atom of a phosphonite; or $X^{23}$ can represent oxygen and $X^{21}$ and $X^{22}$, each a single bond; or $X^{21}$ can represent oxygen and $X^{22}$ and $X^{23}$, each a single bond, so that the phosphorus atom surrounded by $X^{21}, X^{22}$, and $X^{23}$ can be the central atom of a phosphinite; or $X^{21}, X^{22}$, and $X^{23}$ can each represent a single bond, so that the phosphorus atom surrounded by $X^{21}, X^{22}$, and $X^{23}$ can be the central atom of a phosphine.

When the phosphorus atom surrounded by $X^{11}, X^{12}$, and $X^{13}$ is the central atom of a phosphonite and the phosphorus atom surrounded by $X^{21}, X^{22}$, and $X^{23}$ is the central atom of a phosphite, the multidentate ligand represented by Formula I is a phosphite-phosphonite and is an example of a mixed P-containing ligand. When the phosphorus atom surrounded by $X^{11}, X^{12}$, and $X^{13}$ is the central atom of a phosphonite and the phosphorus atom surrounded by $X^{21}, X^{22}$, and $X^{23}$ is the central atom of a phosphonite, the multidentate P-containing ligand represented by Formula I is a phosphonite. When the phosphorus atom surrounded by $X^{11}, X^{12}$, and $X^{13}$ is the central atom of a phosphonite and the phosphorus atom surrounded by $X^{21}, X^{22}$, and $X^{23}$ is the central atom of a phosphinite, the multidentate P-containing ligand represented by Formula I is a phosphinite-phosphonite and is an example of a mixed P-containing ligand. When the phosphorus atom surrounded by $X^{11}, X^{12}$, and $X^{13}$ is the central atom of a phosphonite and the phosphorus atom surrounded by $X^{21}, X^{22}$, and $X^{23}$ is the central atom of a phosphine, the multidentate P-containing ligand represented by Formula I is a phosphonite-phosphine and is an example of a mixed P-containing ligand.

In another embodiment, $X^{13}$ can represent oxygen and $X^{11}$ and $X^{12}$, each a single bond; or $X^{11}$ can represent oxygen and $X^{12}$ and $X^{13}$, each a single bond, so that the phosphorus atom surrounded by $X^{11}, X^{12}$, and $X^{13}$ is the central atom of a phosphinite. In such a case, $X^{21}, X^{22}$, and $X^{23}$ can each represent oxygen, so that the phosphorus atom surrounded by $X^{21}, X^{22}$, and $X^{23}$ can be the central atom of a phosphite; or $X^{23}$ can represent oxygen and $X^{21}$ and $X^{22}$, each a single bond; or $X^{21}$ can represent oxygen and $X^{22}$ and $X^{23}$, each a single bond, so that the phosphorus atom surrounded by $X^{21}, X^{22}$, and $X^{23}$ can be the central atom of a phosphinite; or $X^{21}, X^{22}$, and $X^{23}$ can each represent a single bond, so that the phosphorus atom surrounded by $X^{21}, X^{22}$, and $X^{23}$ can be the central atom of a phosphine.

When the phosphorus atom surrounded by $X^{11}, X^{12}$, and $X^{13}$ is the central atom of a phosphinite and the phosphorus atom surrounded by $X^{21}, X^{22}$, and $X^{23}$ is the central atom of a phosphite, the multidentate P-containing ligand represented by Formula I is a phosphite-phosphinite and is an example of a mixed P-containing ligand. When the phosphorus atom surrounded by $X^{11}, X^{12}$, and $X^{13}$ is the central atom of a phosphinite and the phosphorus atom surrounded by $X^{21}, X^{22}$, and $X^{23}$ is the central atom of a phosphinite, the multidentate P-containing ligand represented by Formula I is a phosphinite. When the phosphorus atom surrounded by $X^{11}, X^{12}$, and $X^{13}$ is the central atom of a phosphinite and the phosphorus atom surrounded by $X^{21}, X^{22}$, and $X^{23}$ is the central atom of a phosphine, the multidentate P-containing ligand represented by Formula I is a phosphinite-phosphine and is an example of a mixed P-containing ligand.

In another embodiment, $X^{11}, X^{12}$, and $X^{13}$ can each represent a single bond, so that the phosphorus atom surrounded by $X^{11}, X^{12}$, and $X^{13}$ is the central atom of a phosphine. In such a case, $X^{21}, X^{22}$, and $X^{23}$ can each represent oxygen, so that the phosphorus atom surrounded by $X^{21}, X^{22}$, and $X^{23}$ can be the central atom of a phosphite; or $X^{21}, X^{22}$, and $X^{23}$ can each represent a single bond, so that the phosphorus atom surrounded by $X^{21}, X^{22}$, and $X^{23}$ can be the central atom of a phosphine.

When the phosphorus atom surrounded by $X^{11}, X^{12}$, and $X^{13}$ is the central atom of a phosphine and the phosphorus atom surrounded by $X^{21}, X^{22}$, and $X^{23}$ is the central atom of a phosphite, the multidentate P-containing ligand represented by Formula I is a phosphite-phosphine and is an example of a mixed P-containing ligand. When the phosphorus atom surrounded by $X^{11}, X^{12}$, and $X^{13}$ is the central atom of a phosphine and the phosphorus atom surrounded by $X^{21}, X^{22}$, and $X^{23}$ is the central atom of a phosphine, the multidentate P-containing ligand represented by Formula I is a phosphine.

Bridging group Y can be aryl groups substituted, for example, with $C_1$ to $C_4$ hydrocarbyl, or halogen such as fluorine, chlorine, or bromine, or halogenated hydrocarbyl such as trifluoromethyl, or aryl such as phenyl, or unsubstituted aryl groups, for example those with 6 to 20 carbon atoms in the aromatic system, for example 2,2'-biphenyl, 1,1'-bi-2-naphthyl, pyrocatechol, or 1,1'-ferrocenyl.

Radicals $R^{11}$ and $R^{12}$ can independently represent identical or different organic radicals. $R^{11}$ and $R^{12}$ can be aryl radicals, for example those containing 6 to 10 carbon atoms, which can be unsubstituted or singly or multiply substituted, for example by $C_1$ to $C_4$ hydrocarbyl, or halogen such as fluorine, chlorine, or bromine, or halogenated hydrocarbyl such as trifluoromethyl, or unsubstituted aryl such as phenyl and naphthyl, or substituted aryl groups.

Radicals $R^{21}$ and $R^{22}$ can independently represent identical or different organic radicals. $R^{21}$ and $R^{22}$ can be aryl radicals, for example those containing 6 to 10 carbon atoms, which can be unsubstituted or singly or multiply substituted, for example by $C_1$ to $C_4$ hydrocarbyl, or halogen such as fluorine, chlorine, or bromine, or halogenated hydrocarbyl such as trifluoromethyl, or unsubstituted aryl such as phenyl and naphthyl, or substituted aryl groups.

Radicals $R^{11}$ and $R^{12}$ can be single or bridged. Radicals $R^{21}$ and $R^{22}$ can also be single or bridged. Radicals $R^{11}$, $R^{12}$, $R^{21}$ and $R^{22}$ can all be single, or two can be bridged and two single, or all four can be bridged in the manner described.

The P-containing ligand can also be a polymeric ligand composition, as disclosed, for example, in U.S. Pat. No. 6,284,865; U.S. Pat. No. 6,924,345, or United States Published Patent Application No. 2003/135014. Methods for preparing such polymeric ligand compositions are well known in the art and are disclosed, for example, in the above cited references.

The catalyst can include at least one monodentate P-containing ligand selected from the group consisting of a phosphite, a phosphonite, a phosphinite, and a phosphine or a combination of such members. The monodentate P-containing ligand can be added as an additional component of the catalyst when a multidentate P-containing ligand is used, or it can be present, for example, as an impurity from the synthesis of the P-containing ligand, or the monodentate P-containing ligand can be used without a multidentate P-containing ligand. The monodentate P-containing ligand can be represented by Formula II, $$P(X^1R^{31})(X^2R^{32})(X^3R^{33}) \qquad \text{Formula II}$$

wherein, $X^1$, $X^2$, $X^3$ independently represent oxygen or a single bond, and $R^{31}$, $R^{32}$, $R^{33}$ independently represent identical or different, single or bridged organic radicals.

It is to be understood that Formula II can represent a single compound or a mixture of different compounds having the indicated formula.

In one embodiment, all of the groups $X^1$, $X^2$, and $X^3$ can represent oxygen, so that Formula II represents a phosphite of formula $P(OR^{31})(OR^{32})(OR^{33})$, wherein $R^{31}$, $R^{32}$, and $R^{33}$ have the meanings defined herein.

If one of the groups $X^1$, $X^2$, and $X^3$ represents a single bond and two groups represent oxygen, Formula II represents a phosphonite of formula $P(OR^{31})(OR^{32})(R^{33})$, $P(R^{31})(OR^{32})(OR^{33})$, or $P(OR^{31})(R^{32})(OR^{33})$, wherein $R^{31}$, $R^{32}$, and $R^{33}$ have the meanings defined herein.

If two of the groups $X^1$, $X^2$, and $X^3$ represent single bonds and one group represents oxygen, Formula II represents a phosphinite of formula $P(OR^{31})(R^{32})(R^{33})$ or $P(R^{31})(OR^{32})(R^{33})$ or $P(R^{31})(R^{32})(OR^{33})$, wherein $R^{31}$, $R^{32}$, and $R^{33}$ have the meanings defined herein.

The groups $X^1$, $X^2$, $X^3$ can independently represent oxygen or a single bond. If all the groups $X^1$, $X^2$, and $X^3$ represent single bonds, Formula II represents a phosphine of formula $P(R^{31})(R^{32})(R^{33})$, wherein $R^{31}$, $R^{32}$, and $R^{33}$ have the meanings defined herein.

Radicals $R^{31}$, $R^{32}$, and $R^{33}$ can independently represent identical or different organic radicals, for example hydrocarbyl radicals including 1 to 20 carbon atoms, such as methyl, ethyl, normal-propyl, iso-propyl, normal-butyl, iso-butyl, sec-butyl, and tert-butyl, aryl groups such as phenyl, o-tolyl, m-tolyl, p-tolyl, 1-naphthyl, or 2-naphthyl. The $R^{31}$, $R^{32}$, and $R^{33}$ radicals can be connected to one another directly, meaning not solely via the central phosphorus atom. For example, the monodentate phosphites of Formula I within U.S. Pat. No. 5,543,536 and monodentate phosphonites of Formula I within U.S. Pat. No. 6,242,633. Alternatively, the $R^{31}$, $R^{32}$, and $R^{33}$ radicals can be not directly connected to one another.

For example, $R^{31}$, $R^{32}$, and $R^{33}$ can be selected from the group composed of phenyl, o-tolyl, m-tolyl, and p-tolyl. As another example, a maximum of two of the $R^{31}$, $R^{32}$, and $R^{33}$ groups can be phenyl. Alternatively, a maximum of two of the $R^{31}$, $R^{32}$, and $R^{33}$ groups can be o-tolyl.

Compounds of Formula IIa, $$(o\text{-tolyl-O—})_w(m\text{-tolyl-O—})_x(p\text{-tolyl-O—})_y(\text{phenyl-O—})_zP \qquad \text{Formula IIa}$$

can be used as the monodentate P-containing ligand, wherein w, x, y, and z are integers, and the following conditions apply: $w+x+y+z=3$ and $w, z \leq 2$.

Examples of compounds of Formula IIa include (p-tolyl-O—)(phenyl-O—)$_2$P, (m-tolyl-O—)(phenyl-O—)$_2$P, (o-tolyl-O—)(phenyl-O—)$_2$P, (p-tolyl-O—)$_2$(phenyl-O—)P, (m-tolyl-O—)2(phenyl-O—)P, (o-tolyl-O—)$_2$(phenyl-O—)P, (m-tolyl-O—)(p-tolyl-O—)(phenyl-O—)P, (o-tolyl-O—)(p-tolyl-O—)(phenyl-O—)P, (o-tolyl-O—)(m-tolyl-O—)(phenyl-O—)P, (p-tolyl-O—)$_3$P, (m-tolyl-O—)(p-tolyl-O—)$_2$P, (o-tolyl-O—)(p-tolyl-O—)$_2$P, (m-tolyl-O—)$_2$(p-tolyl-O—)P, (o-tolyl-O—)$_2$(p-tolyl-O—)P, (o-tolyl-O—)(m-tolyl-O—)(p-tolyl-O—)P, (m-tolyl-O—)$_3$P, (o-tolyl-O—)(m-tolyl-O—)$_2$P, (o-tolyl-O—)$_2$(m-tolyl-O—)P, or mixtures of such compounds.

Mixtures containing (m-tolyl-O—)$_3$P, (m-tolyl-O—)$_2$(p-tolyl-O—)P, (m-tolyl-O—)(p-tolyl-O—)$_2$P, and (p-tolyl-O—)$_3$P can be obtained, for example, by reacting a mixture containing m-cresol and p-cresol, in particular in a molar ratio of 2:1 as occurs in the distillative processing of crude oil, with a phosphorus trihalide such as phosphorus trichloride.

Additional examples of monodentate P-containing ligands are the phosphites disclosed in U.S. Pat. No. 6,770,770 and referred to herein as phosphites of Formula IIb, $$P(OR^{31})_x(OR^{32})_y(OR^{33})_z(OR^{34})_p \qquad \text{Formula IIb}$$

wherein, $R^{31}$ is an aromatic radical having a $C_1$ to $C_{18}$ alkyl substituent in the o-position relative to the oxygen atom which connects the phosphorus atom to the aromatic system, or having an aromatic substituent in the o-position relative to the oxygen atom which connects the phosphorus atom to the aromatic system, or having an aromatic system fused on in the o-position relative to the oxygen atom which connects the phosphorus atom to the aromatic system;

$R^{32}$ is an aromatic radical having a $C_1$ to $C_{18}$ alkyl substituent in the m-position relative to the oxygen atom which connects the phosphorus atom to the aromatic system, or having an aromatic substituent in the m-position relative to the oxygen atom which connects the phosphorus atom to the aromatic system, or having an aromatic system fused on in the m-position relative to the oxygen atom which connects the phosphorus atom to the aromatic system, where the aromatic radical bears a hydrogen atom in the o-position relative to the oxygen atom which connects the phosphorus atom to the aromatic system;

$R^{33}$ is an aromatic radical having a $C_1$ to $C_{18}$ alkyl substituent in the p-position relative to the oxygen atom which connects the phosphorus atom to the aromatic system, or having an aromatic substituent in the p-position relative to the oxygen atom which connects the phosphorus atom to the aromatic system, where the aromatic radical bears a hydrogen atom in the o-position relative to the oxygen atom which connects the phosphorus atom to the aromatic system;

$R^{34}$ is an aromatic radical which bears substituents other than those defined for $R^{31}$, $R^{32}$, and $R^{33}$ in the o-, m-, and p-position relative to the oxygen atom which connects the phosphorus atom to the aromatic system, where the aromatic radical bears a hydrogen atom in the o-position relative to the oxygen atom which connects the phosphorus atom to the aromatic system;

x is 1 or 2; and y, z, and p independently of one another are 0, 1, or 2, provided that x+y+z+p=3.

Examples of radical $R^{31}$ include o-tolyl, o-ethylphenyl, o-normal-propylphenyl, o-iso-propylphenyl, o-normal-butylphenyl, o-sec-butylphenyl, o-tert-butylphenyl, (o-phenyl)phenyl, or 1-naphthyl groups.

Examples of radical $R^{32}$ include m-tolyl, m-ethylphenyl, m-normal-propylphenyl, m-iso-propylphenyl, m-normal-butylphenyl, m-sec-butylphenyl, m-tert-butylphenyl, (m-phenyl)-phenyl, or 2-naphthyl groups.

Examples of radical $R^{33}$ include p-tolyl, p-ethylphenyl, p-normal-propylphenyl, p-iso-propylphenyl, p-normal-butylphenyl, p-sec-butylphenyl, p-tert-butylphenyl, or (p-phenyl)phenyl groups. Radical $R^{34}$ can be, for example, phenyl.

The indices x, y, z, and p in compounds of Formula IIb can have the following possibilities:

| x | y | z | p |
|---|---|---|---|
| 1 | 0 | 0 | 2 |
| 1 | 0 | 1 | 1 |
| 1 | 1 | 0 | 1 |
| 2 | 0 | 0 | 1 |
| 1 | 0 | 2 | 0 |
| 1 | 1 | 1 | 0 |
| 1 | 2 | 0 | 0 |
| 2 | 0 | 1 | 0 |
| 2 | 1 | 0 | 0 |

Examples of phosphites of Formula IIb are those in which p is zero, and $R^{31}$, $R^{32}$, and $R^{33}$ are independently selected from o-iso-propylphenyl, m-tolyl, and p-tolyl.

Additional examples of phosphites of Formula IIb are those in which $R^{31}$ is the o-iso-propylphenyl radical, $R^{32}$ is the m-tolyl radical, and $R^{33}$ is the p-tolyl radical, with the indices listed in the above table; also those in which $R^{31}$ is the o-tolyl radical, $R^{32}$ is the m-tolyl radical, and $R^{33}$ is the p-tolyl radical, with the indices listed in the table; also those in which $R^{31}$ is the 1-naphthyl radical, $R^{32}$ is the m-tolyl radical, and $R^{33}$ is the p-tolyl radical, with the indices listed in the table; also those in which $R^{31}$ is the o-tolyl radical, $R^{32}$ is the 2-naphthyl radical, and $R^{33}$ is the p-tolyl radical, with the indices listed in the table; and lastly, those in which $R^{31}$ is the o-iso-propylphenyl radical, $R^{32}$ is the 2-naphthyl radical, and $R^{33}$ is the p-tolyl radical, with the indices listed in the table; and mixtures of these phosphites.

Phosphites having the Formula IIb can be obtained as follows:

a). phosphorus trihalide is reacted with an alcohol selected from the group including $R^{31}OH$, $R^{32}OH$, $R^{33}OH$ and $R^{34}OH$ or mixtures thereof to obtain a dihalogenophosphoric acid monoester, b). the aforementioned dihalogenophosphoric acid monoesters are reacted with an alcohol selected from the group including $R^{31}OH$, $R^{32}OH$, $R^{33}OH$ and $R^{34}OH$ or mixtures thereof to obtain a monohalogenophosphoric acid diester, and c). the aforementioned monohalogenophosphoric acid diester is reacted with an alcohol selected from the group including $R^{31}OH$, $R^{32}OH$, $R^{33}OH$ and $R^{34}OH$ or mixtures thereof to obtain a phosphite having the Formula IIb.

The reaction can be performed in three separate steps. It is also possible to combine two of the three steps, for example a) with b) or b) with c). Alternatively, all steps a), b), and c) can be combined with each other.

Suitable parameters and quantities of the alcohols selected from the group including $R^{31}OH$, $R^{32}OH$, $R^{33}OH$ and $R^{34}OH$ or mixtures thereof can be easily determined by conducting a few simple preliminary experiments. Published patent application WO2004/050588 describes methods for the selective synthesis of organophosphites having the Formula IIb.

Suitable phosphorus trihalides are in principle all phosphorus trihalides in which preferable Cl, Br, I, particularly Cl is used as the halide, as well as mixtures thereof. It is also possible to use mixtures of different equally or differently halogen-substituted phosphines as the phosphorus trihalide, for example $PCl_3$. Further details regarding the reaction conditions during the production of phosphites of Formula IIb and regarding the treatment are disclosed in U.S. Pat. No. 6,770,770.

Phosphites of Formula IIb can also be used as a mixture of different phosphites as ligand. Such a mixture can be formed, for example, in the preparation of phosphites of Formula IIb.

In one embodiment of the process of the invention, the P-containing ligand of the catalyst and/or the free P-containing ligand is selected from at least one multidentate P-containing ligand selected from the group consisting of a phosphite, a phosphonite, a phosphinite, a phosphine, and a mixed P-containing ligand or a combination of such members, and at least one monodentate P-containing ligand selected from tritolyl phosphite and the phosphites of Formula IIb wherein $R^{31}$, $R^{32}$, and $R^{33}$ are independently selected from o-isopropylphenyl, m-tolyl, and p-tolyl, $R^{34}$ is phenyl, x is 1 or 2, and y, z, and p are independently 0, 1, or 2, provided that x+y+z+p=3; and mixtures thereof.

Examples of multidentate P-containing ligands include the following:

1) the compounds of Formulae I, II, III, IV, and V disclosed in U.S. Pat. No. 5,723,641;

2) the compounds of Formulae I, II, III, IV, V, VI, and VII disclosed in U.S. Pat. No. 5,512,696, for example the compounds used in Examples 1 through 31 therein;

3) the compounds of Formulae I, II, III, IV, V, VI, VII, VIII, IX, X, XI, XII, XIII, XIV, and XV disclosed in U.S. Pat. No. 5,821,378, for example the compounds used in Examples 1 through 73 therein;

4) the compounds of Formulae I, II, III, IV, V, and VI disclosed in U.S. Pat. No. 5,512,695, for example the compounds used in Examples 1 through 6 therein;

5) the compounds of Formulae I, II, III, IV, V, VI, VII, VIII, IX, X, XI, XII, XIII, and XIV disclosed in U.S. Pat. No. 5,981,772, for example the compounds used in Examples 1 through 66 therein;

6) the compounds disclosed in U.S. Pat. No. 6,127,567, for example the compounds used in Examples 1 through 29 therein;

7) the compounds of Formulae I, II, III, IV, V, VI, VII, VIII, IX, and X disclosed in U.S. Pat. No. 6,020,516, for example the compounds used in Examples 1 through 33 therein;

8) the compounds disclosed in U.S. Pat. No. 5,959,135, for example the compounds used in Examples 1 through 13 therein;

9) the compounds of Formulae I, II, and III disclosed in U.S. Pat. No. 5,847,191;

10) the compounds disclosed in U.S. Pat. No. 5,523,453, for example the compounds of Formulae 1, 2, 3, 4, 5, 6, 7, 8, 9, 10, 11, 12, 13, 14, 15, 16, 17, 18, 19, 20, and 21 therein;

11) the compounds disclosed in U.S. Pat. No. 5,693,843, for example the compounds of Formulae I, II, III, IV, V, VI, VII, VIII, IX, X, XI, XII, and XIII, for example the compounds used in Examples 1 through 20 therein;

12) the compounds of Formulae V, VI, VII, VIII, IX, X, XI, XII, XIII, XIV, XV, XVI, XVII, XVIII, XIX, XX, XXI, XXII, XXIII, XXIV, XXV, and XXVI disclosed in U.S. Pat. No. 6,893,996;

13) the compounds disclosed in published patent application WO 01/14392, for example the compounds illustrated in Formulae V, VI, VII, VIII, IX, X, XI, XII, XIII, XIV, XV, XVI, XVII, XXI, XXII, and XXIII therein;

14) the chelating compounds disclosed in U.S. Pat. No. 6,242,633, for example the compounds of Formulae If, Ig, and Ih;

15) the compounds disclosed in U.S. Pat. No. 6,521,778, for example the compounds of Formulae I, Ia, Ib, and Ic, for example the compounds referred to as Ligand I and II;

16) the compounds disclosed in published PCT patent application WO 02/13964, for example the compounds of Formulae Ia, Ib, Ic, Id, Ie, If, Ig, Ih, Ii, Ij, and Ik, for example the compounds referred to as Ligand 1, 2, 3, 4, 5, and 6;

17) the compounds disclosed in German Patent Application DE 100 460 25;

18) the chelating compounds disclosed in U.S. Pat. No. 7,022,866, for example the compounds of Formulae 1 and 2, for example the compounds referred to as Ligand 1 and 2;

19) the compounds disclosed in United States Published Patent Application No. 2005/0090677, for example the compounds of Formulae 1, 1a, 1b, 1c, 1d, 1e, 1f, 1g, 1h, 1i, 1j, 1k, 1l, 1m, 1n, 1o, 2, and 3;

20) the compounds disclosed in U.S. Pat. No. 7,067,685, for example the compounds of Formulae 1 and 2, for example the compounds referred to as Ligand 1, 2, 3, 4, 5, and 6;

21) the compounds disclosed in United States Published Patent Application No. 2007/0060766, for example the compounds of Formulae 1, 1a, 1b, 1c, 1d, 1e, 1f, 1g, 1h, 1i, 1j, 1k, 1l, 1m, 1n, 1o, 2, 3, 4, 5, and 6, for example the compounds referred to as Ligand 1, 2, 3, and 4;

22) the chelating compounds disclosed in U.S. Pat. No. 6,169,198, for example the compounds of Formula I;

23) the compounds disclosed in U.S. Pat. No. 6,660,877, for example the compounds of Formulae I, II, and III, for example the compounds used in Examples 1 through 27 therein;

24) the compounds disclosed in U.S. Pat. No. 6,197,992, for example the compounds of Ligand A and B;

25) the compounds disclosed in U.S. Pat. No. 6,242,633, for example the compounds of Formulae I, Ia, Ib, Ic, Id, Ie, If, Ig, and Ih;

26) the compounds disclosed in U.S. Pat. No. 6,812,352, for example the compounds of Formula I; and, 27) the compounds disclosed in U.S. Pat. No. 6,380,421, for example the compounds of Example 1, 2 and 3.

28) The bidentate phosphine of structure 5 in Laura Bini, et. al., *J. Am. Chem. Soc.* 2007, 129, 12622-12623.

These references also disclose methods for preparing multidentate ligands of Formula I.

Additional examples of ligands which, in combination with nickel, form highly active catalysts for the hydrocyanation of 1,3-butadiene or 3-pentenenitrile and the isomerization of 2-methyl-3-butenenitrile to 3-pentenenitrile are bidentate phosphite ligands of the following structural formulae:

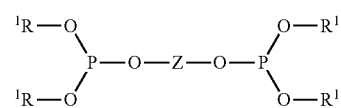

Formula IIIa

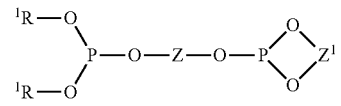

Formula IIIb

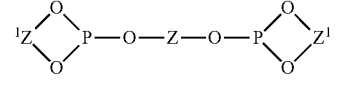

Formula IIIc wherein in Formulae IIIa, IIIb, and IIIc, $R^1$ is phenyl, unsubstituted or substituted with one or more $C_1$ to $C_{12}$ alkyl, $C_1$ to $C_{12}$ alkoxy groups, or groups of Formulae A and B, or —$(CH_2)_nOY^2$; or naphthyl, unsubstituted or substituted with one or more $C_1$ to $C_{12}$ alkyl or $C_1$ to $C_{12}$ alkoxy groups, or groups of Formulae A and B, or —$(CH_2)_nOY^2$; or 5,6,7,8-tetrahydro-1-naphthyl;

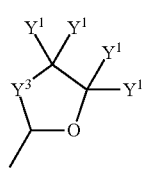

Formula A

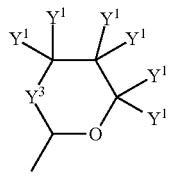

Formula B wherein, $Y^1$ is independently selected from the group of H, $C_1$ to $C_{18}$ alkyl, cycloalkyl, or aryl, $Y^2$ is independently selected from the group of $C_1$ to $C_{18}$ alkyl, cycloalkyl, or aryl, $Y^3$ is independently selected from the group of O or $CH_2$, and n=1 to 4;

and O—Z—O and O—$Z^1$—O are independently selected from the group consisting of structural Formulae IV, V, VI, VII, and VIII:

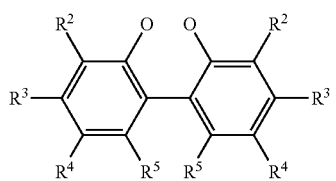

IV

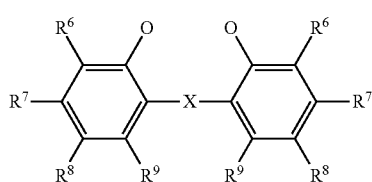

V and wherein

R², R³, R⁴, R⁵, R⁶, R⁷, R⁸, and R⁹ are independently selected from the group consisting of H, $C_1$ to $C_{12}$ alkyl, and $C_1$ to $C_{12}$ alkoxy; X is O, S, or $CH(R^{10})$;

$R^{10}$ is H or $C_1$ to $C_{12}$ alkyl;

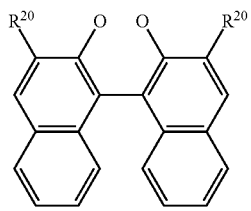

VI

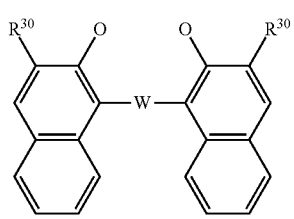

VII and wherein $R^{20}$ and $R^{30}$ are independently selected from the group consisting of H, $C_1$ to $C_{12}$ alkyl, and $C_1$ to $C_{12}$ alkoxy, and $CO_2R^{13}$;

$R^{13}$ is $C_1$ to $C_{12}$ alkyl or $C_6$ to $C_{10}$ aryl, unsubstituted or substituted with $C_1$ to $C_4$ alkyl;

W is O, S, or $CH(R^{14})$;

$R^{14}$ is H or $C_1$ to $C_{12}$ alkyl;

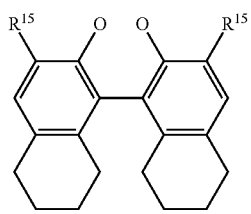

VIII and wherein, $R^{15}$ is selected from the group consisting of H, $C_1$ to $C_{12}$ alkyl, and $C_1$ to $C_{12}$ alkoxy and $CO_2R^{16}$;

$R^{16}$ is $C_1$ to $C_{12}$ alkyl or $C_6$ to $C_{10}$ aryl, unsubstituted or substituted with $C_1$ to $C_4$ alkyl.

In the structural Formulae IIIa, IIIb, IIIc, and IV through VIII, the $C_1$ to $C_{12}$ alkyl, and $C_1$ to $C_{12}$ alkoxy groups can be straight chain or branched.

It is to be understood that structural Formulae IIIa, IIIb, and IIIc can represent a single compound or a mixture of different compounds having the indicated formulae.

Examples of bidentate phosphite ligands that are useful in the present process include those having the Formulae IX to XXXII, shown below wherein for each formula, $R^{17}$ is selected from the group consisting of methyl, ethyl or iso-propyl, and $R^{18}$ and $R^{19}$ are independently selected from H or methyl:

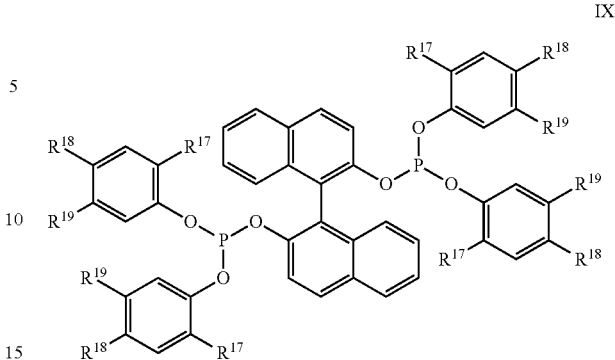

IX

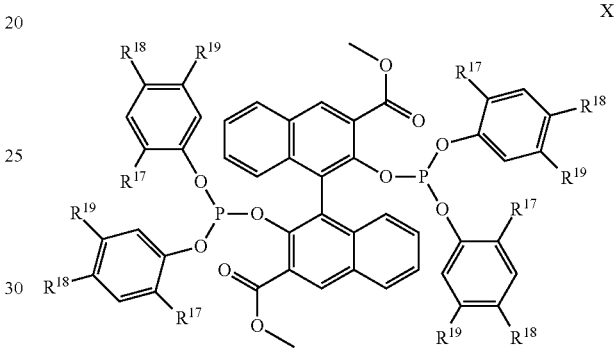

X

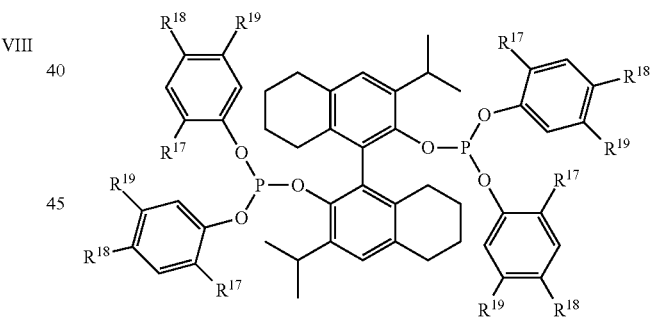

XI

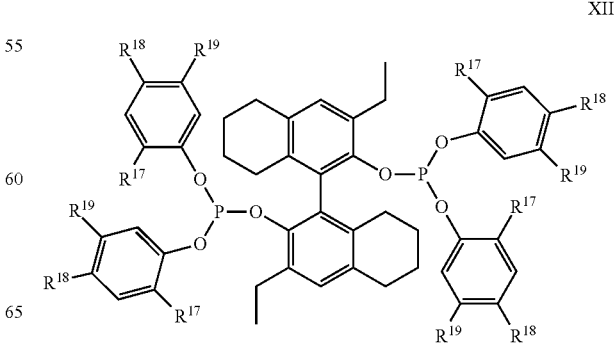

XII

XIII
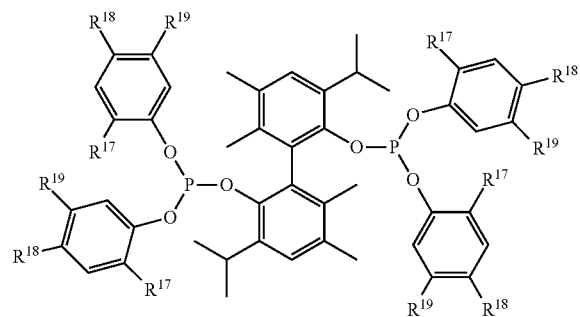
XVII
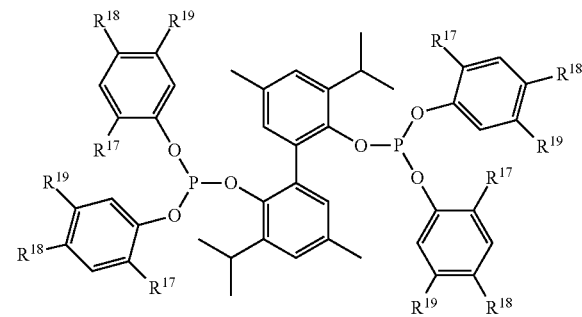
XIV
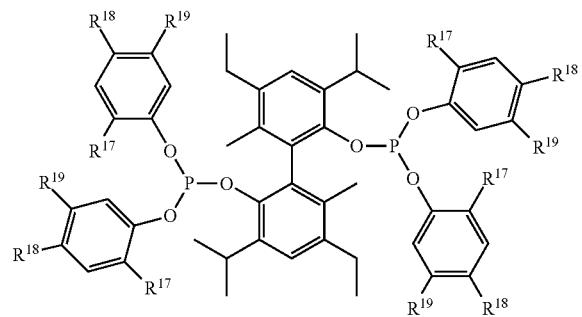
XVIII
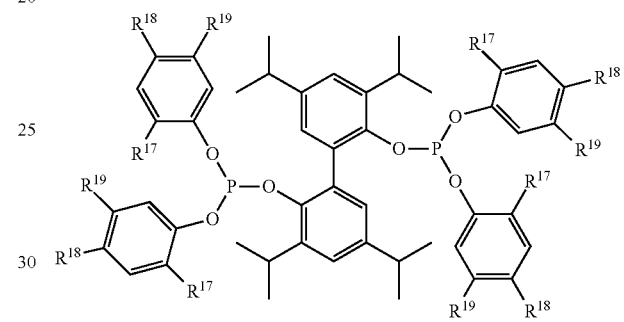
XV
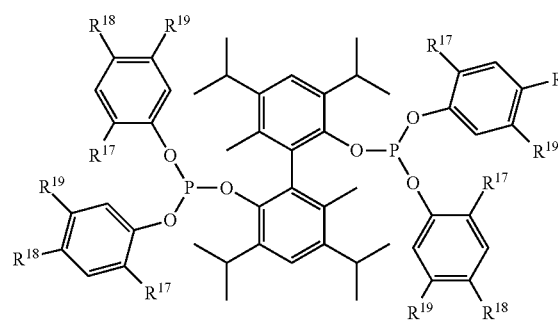
XI
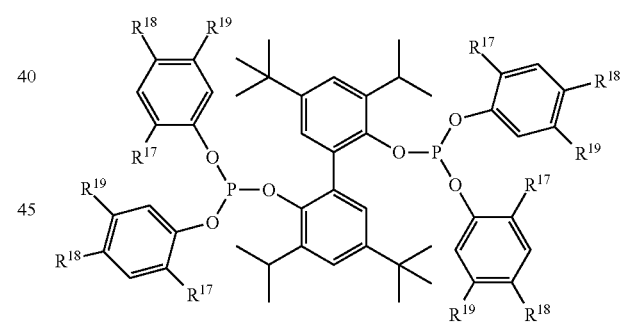
XVI
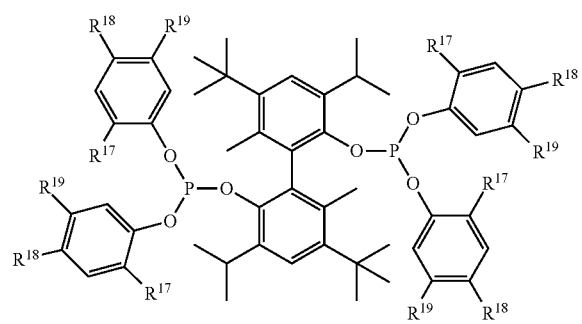
XXX
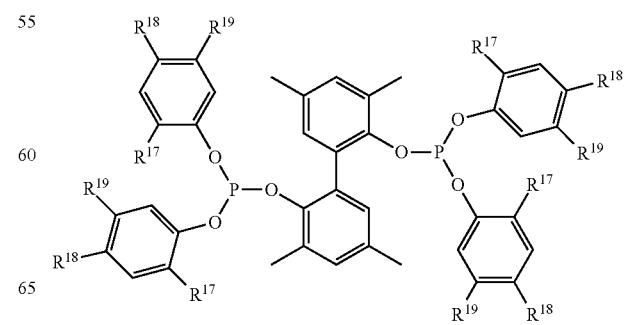

XXI
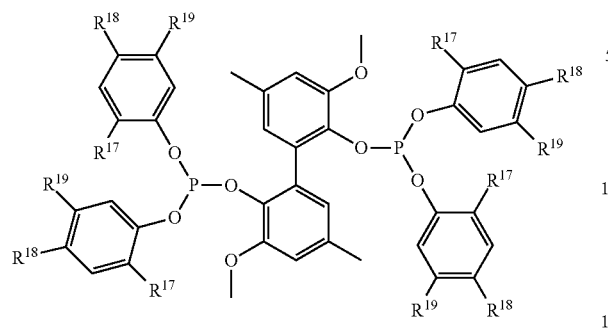
XXV
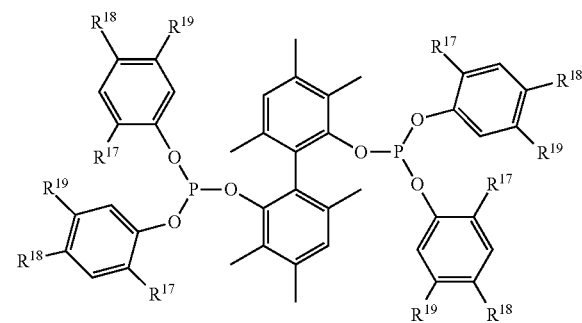
XXII
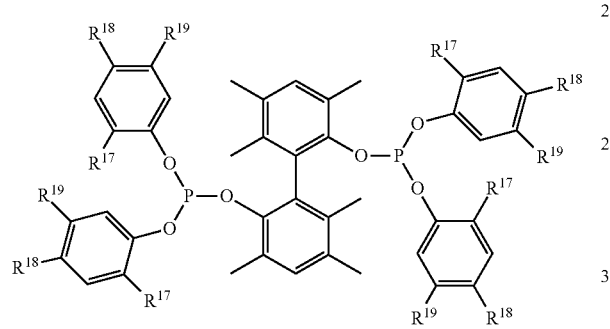
XXVI
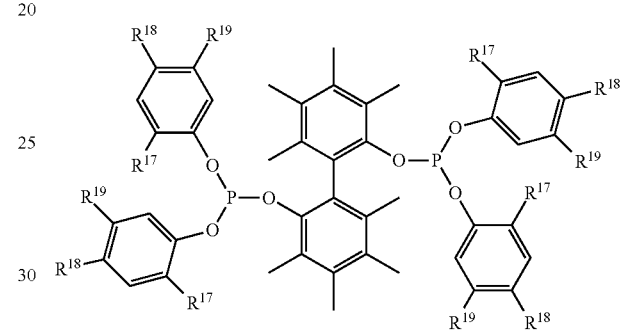
XXIII
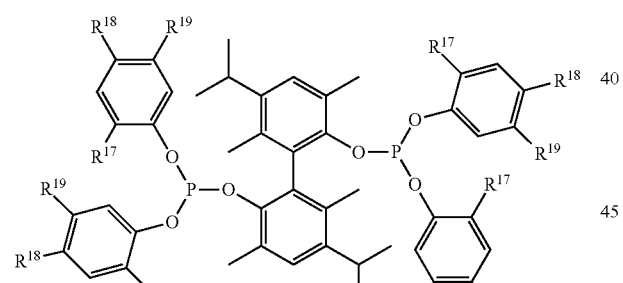
XXVII
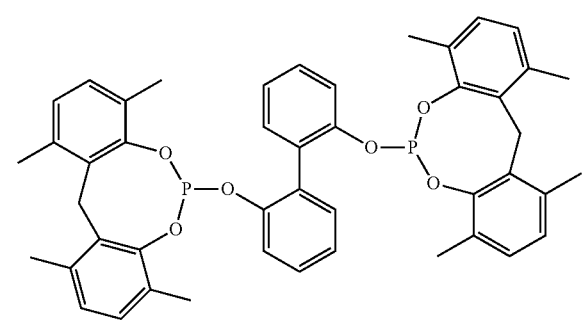
XXIV
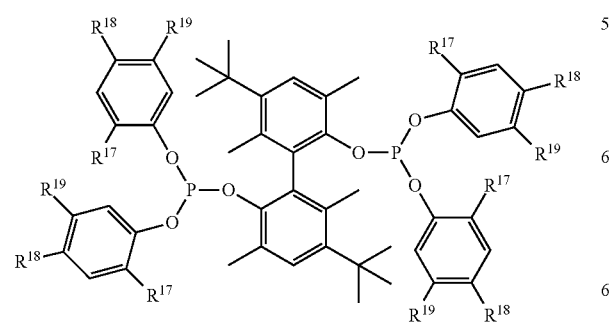
XXVIII
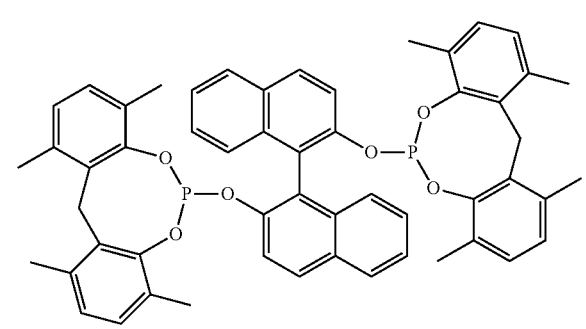

XXIX

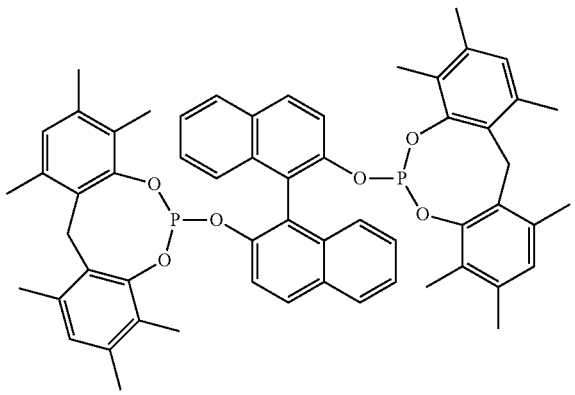

XXX

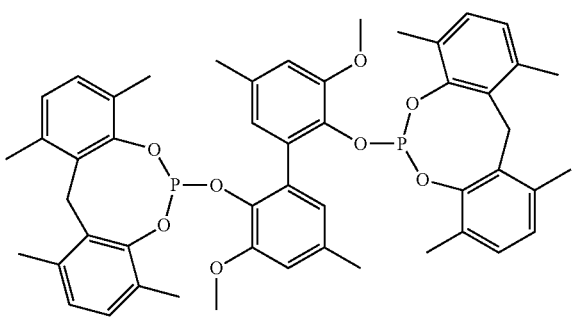

XXXI

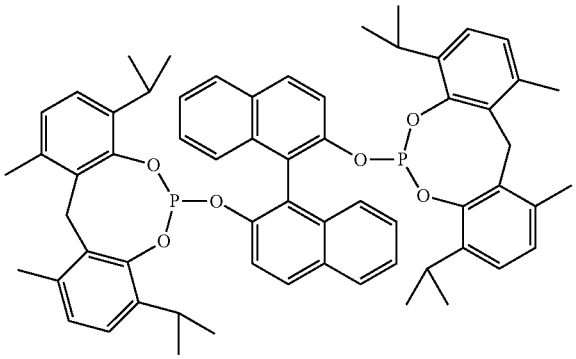

XXXII

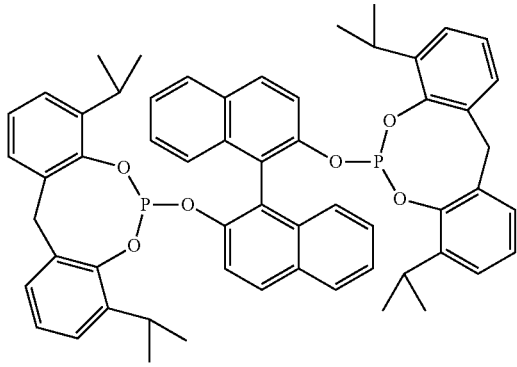

Additional examples of bidentate phosphite ligands that are useful in the present process include a ligand selected from a member of the group represented by Formulae XXXIII and XXXIV, in which all like reference characters have the same meaning, except as further explicitly limited:

Formula XXXIII

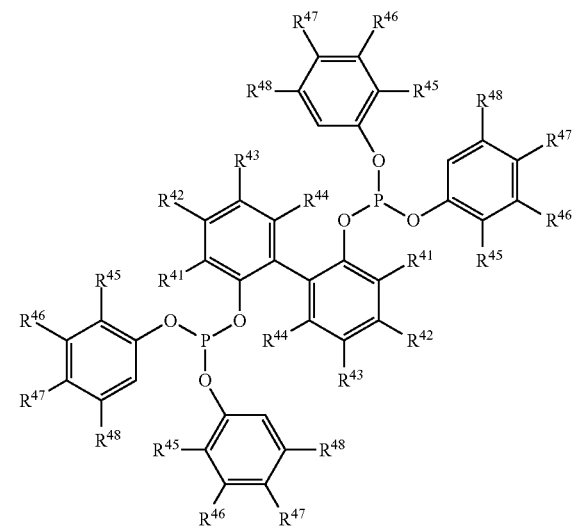

Formula XXXIV

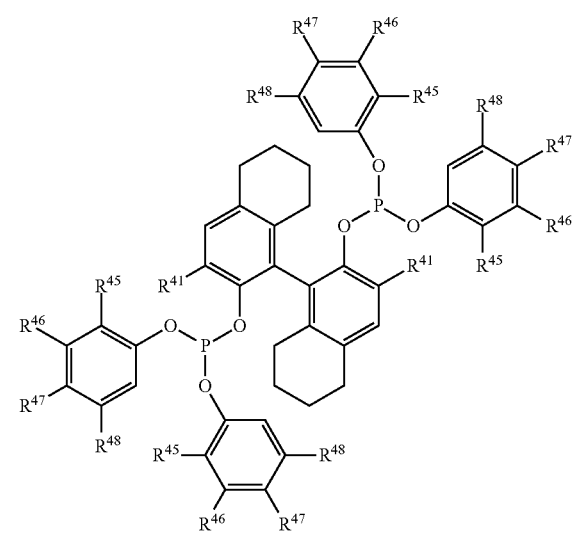

wherein,
$R^{41}$ and $R^{45}$ are independently selected from the group consisting of $C_1$ to $C_5$ hydrocarbyl, and each of $R^{42}$, $R^{43}$, $R^{44}$, $R^{46}$, $R^{47}$ and $R^{48}$ is independently selected from the group consisting of H and $C_1$ to $C_4$ hydrocarbyl.

For example, the bidentate phosphite ligand can be selected from a member of the group represented by Formula XXXIII and Formula XXXIV, wherein
$R^{41}$ is methyl, ethyl, isopropyl or cyclopentyl;
$R^{42}$ is H or methyl;
$R^{43}$ is H or a $C_1$ to $C_4$ hydrocarbyl;
$R^{44}$ is H or methyl;
$R^{45}$ is methyl, ethyl or isopropyl; and
$R^{46}$, $R^{47}$ and $R^{48}$ are independently selected from the group consisting of H and $C_1$ to $C_4$ hydrocarbyl.

As additional examples, the bidentate phosphite ligand can be selected from a member of the group represented by Formula XXXIII, wherein
$R^{41}$, $R^{44}$, and $R^{45}$ are methyl;
$R^{42}$, $R^{46}$, $R^{47}$ and $R^{48}$ are H; and
$R^{43}$ is a $C_1$ to $C_4$ hydrocarbyl; or $R^{41}$ is isopropyl;
$R^{42}$ is H;
$R^{43}$ is a $C_1$ to $C_4$ hydrocarbyl;
$R^{44}$ is H or methyl;
$R^{45}$ is methyl or ethyl;
$R^{46}$ and $R^{48}$ are H or methyl; and
$R^{47}$ is H, methyl or tertiary-butyl;
or the bidentate phosphite ligand can be selected from a member of the group represented by Formula XXXIV, wherein
$R^{41}$ is isopropyl or cyclopentyl;
$R^{45}$ is methyl or isopropyl; and
$R^{47}$, and $R^{48}$ are H.

As yet another example, the bidentate phosphite ligand can be represented by Formula XXXIII, wherein $R^{41}$ is isopropyl; $R^{42}$, $R^{46}$, and $R^{48}$ are H; and $R^{43}$, $R^{44}$, $R^{45}$, and $R^{47}$ are methyl.

It will be recognized that Formulae IX to XXXIV are two-dimensional representations of three-dimensional molecules and that rotation about chemical bonds can occur in the molecules to give configurations differing from those shown. For example, rotation about the carbon-carbon bond between the 2- and 2'-positions of the biphenyl, octahydrobinaphthyl, and or binaphthyl bridging groups of Formulae IX to XXXIV, respectively, can bring the two phosphorus atoms of each Formula in closer proximity to one another and can allow the phosphite ligand to bind to nickel in a bidentate fashion. The term "bidentate" is well known in the art and means both phosphorus atoms of the ligand are bonded to a single nickel atom.

The P-containing ligands useful in the present invention can be prepared by any suitable synthetic means known in the art. For example, in general the multidentate P-containing ligands can be synthesized analogously to the method described in U.S. Pat. Nos. 6,171,996 and 5,512,696, both of which are incorporated herein by reference. For example, the reaction of two equivalents of an ortho-substituted phenol with phosphorus trichloride gives the corresponding phosphorochloridite. The reaction of the phosphorochloridite with the desired unsubstituted or substituted biphenol, octahydrobinaphthol, or binaphthol in the presence of triethylamine gives the bidentate phosphite ligand. The crude bidentate phosphite ligand can be worked up by the processes described in U.S. Pat. Nos. 6,069,267 and 6,844,249, which are incorporated herein by reference. As disclosed therein, the bidentate phosphite ligand product mixture can typically contain the desired product in about 70% to about 90% selectivity, with other phosphite by-products such as monodentate phosphites making up the balance of the product mixture.

The multidentate P-containing ligand itself, mixtures of the multidentate P-containing ligand and at least one monodentate P-containing ligand, or at least one monodentate P-containing ligand itself are suitable for use with the present invention.

BNC Nickel

In some embodiments of the method of the present invention, the source of the Ni(II) of the nickel composition of step (ii) is basic nickel carbonate, also referred to as BNC nickel. In an example, BNC can be described with a chemical formula of $[Ni(CO_3)_x(OH)_y]_z(H_2O)_n$, wherein $x=z-(y/2)$; $y=2z-2x$; $z=1$ to 100; and $n=0$ to 400. BNC can be referred to as including nickel(II) ions, carbonate ions, hydroxide ions, and water molecules. In one example, the BNC nickel is acquired through a commercial source. In another example, the BNC nickel is synthesized using other sources of Ni(II). The BNC nickel can be synthesized using the procedures disclosed herein. Certain forms of BNC nickel, including BNC nickel generated by some of the procedures detailed herein, can yield a Ni(0) that is particularly well-suited to formation of nickel(0) complexes with phosphorus-containing ligands, and can be particularly well-suited to the method of forming a nickel complex including nickel and at least one phosphorus-containing ligand disclosed herein. Ni(0) that is particularly well-suited to forming a nickel complex including nickel and at least one phosphorus-containing ligand includes Ni(0) that gives higher rates of formation of the nickel complex. Features of the Ni(0) that is well-suited to forming a nickel complex including nickel and at least one phosphorus-containing ligand include, for example, low carbon content, large surface area, small crystallite size (e.g. less than 89 nm), and optionally a broad size distribution. Ni(0) can have a surface area of, for example, about 0.5 square meters per gram, 2 $m^2/g$, 4, 6, 10, 20, 30, 40, about 50 $m^2/g$, or any value in between. In some examples, Ni(0) with a surface area greater than about 2 $m^2/g$, 5 $m^2/g$, 10 $m^2/g$, 20 $m^2/g$ or greater than about 30 $m^2/g$ are particularly well-suited to forming nickel complexes with phosphorus-containing ligands. BNC nickel that has features including, for example, low carbonate content, a molar ratio of $NiCO_3:Ni(OH)_2$<approximately 1, with a mass ratio of Ni:C of at least about 10:1, or any combination thereof, can produce Ni(0) with low levels of carbon impurities, including carbon impurities due to carbonate impurities, and thus produces Ni(0) that is well-suited to nickel-ligand complex formation. The calcination or heating or BNC nickel having features including a low carbonate content, a molar ratio of $NiCO_3:Ni(OH)_2$<approximately 1, with a mass ratio of Ni:C of at least about 10:1, or any combination thereof, more readily produces $CO_2$, and thus causes more complete conversion to NiO, with fewer carbon impurities in the NiO, including carbonate impurities. By producing NiO that has a lower carbon content, including a lower carbonate content, less carbon impurities result in the Ni(0) product.

Disclosed are novel nickel-containing solids including nickel metal, derived from nickel compositions of basic nickel carbonates, and methods of making the same. The nickel compositions can be made by contacting a precipitant solution to a nickel solution in a precipitation reactor to form a reaction mixture; and (ii) precipitating said nickel composition from said reaction mixture, wherein said nickel solution includes nickel(II) ions and water and said precipitant solution is selected from the group consisting of: (a) bicarbonate ions and water, (b) carbonate ions and water, and (c) mixtures thereof. The mole ratio of bicarbonate ions to nickel ions in the reaction mixture at the conclusion of said feeding can range from 0.5:1 to 2:1, including from about 0.5:1 to about 1.6:1, from about 0.5:1 to about 1.2:1, from about 1:1 to about 1.9:1, from about 1.2:1 to about 1.9:1, from about 0.8:1 to about 1.4:1, from about 1:1 to about 1.8:1, from about 1.0:1 to about 1.6:1, from about 1:1 to about 1.4:1, from about 0.8:1 to about 1.4:1, and from about 0.8:1 to about 1.2:1. The mole ratio of carbonate ions to nickel ions in the reaction mixture at the conclusion of said feeding can range from 0.3:1 to 1.6:1, including from about 0.5:1 to about 1.4:1, from about 1:1 to about 1.2:1, from about 0.8:1 to about 1.4:1, from about 1.0:1 to about 1.6:1, from about 1.0:1 to about 1.6:1, from about 1.0:1 to about 1.4:1, from about 0.8:1 to about 1.4:1, and from about 0.8:1 to about 1.2:1. Blends of bicarbonates and carbonates can also be used in the precipitant solution. As detailed more fully below, the molar ratio has a surprising effect on the resulting nickel metal's effectiveness of reacting with the phosphorus ligands.

The precipitation reactor can be any suitable containment vessel such as a tank or pipe. The precipitation can be performed in a batch or continuous fashion. Further, the reaction mixture can be agitated prior to and/or during the precipitation of the nickel composition. For example, agitation can be done by mechanical stirring, pumped circulation loop, or flow-through a static mixer. The use of high sheer during precipitation can prevent particle agglomeration and can give smaller resulting BNC nickel particles. Reactor designs, stirring designs, and the application of high amounts of power to stirring are examples of factors that can cause a high-sheer stirring of the reaction mixture during precipitation. The nickel composition can be precipitated within a temperature range of from about 0° C. to about 90° C., including from about 20° C. to about 90° C., from about 20° C. to about 70° C., from about 20° C. to about 50° C., from about 50° C. to about 90° C., from about 60° C. to about 80° C., and from about 65° C. to about 75° C. In some embodiments, increased temperature during precipitation can decrease the proportion of carbonate ions in the resulting BNC nickel. Furthermore, the nickel composition can be precipitated from the reaction mixture in the presence of added carbon dioxide. For example, the carbon dioxide can be added to the precipitation reactor, added to the nickel solution, added to the precipitant solution, or added to the reaction mixture, and any combination thereof. Also, the precipitant solution can be fed to the precipitation reactor over a period of from about 30 minutes to about 60 minutes, and can be done in a semi-continuous or continuous manner. Further, the precipitant solution can be added to the nickel solution in the precipitation reactor in a semi-continuous or continuous manner, for example, gradual addition. In some embodiments, the use of a higher pH during precipitation can decrease the proportion of carbonate ions in the resulting BNC nickel precipitate. For example, a pH value of about 4, 5, 6 or about 7 can be used. In one example, the pH increases from about 4.9 to about 5.8 during the precipitation.

The reaction mixture can also be digested after contacting the precipitant solution to the nickel solution by heating the reaction mixture from between about 50° C. and about 90° C. for a period of from about 0.25 hours to about 24 hours. Other suitable temperature ranges include from about 60° C. to about 80° C. and from about 65° C. to about 75° C. Other suitable time periods can range from about 1 hours to about 24 hours, including from about 4 hours to about 20 hours, from about 6 hours to about 16 hours, from about 1 to about 6 hours, and from about 1 hour to about 2 hours. In some embodiments, longer digestion times can cause larger BNC nickel particles in the resulting precipitate.

The disclosed nickel composition methods can further include, after the precipitation step, washing the precipitated nickel composition with water; and partially drying the precipitated nickel composition. For example, the precipitated nickel composition from the reaction mixture is separated from the reaction mixture by filtration or decantation, the resulting precipitated nickel composition is washed with water by filtration or decantation, and the resulting precipitated nickel composition is dried by water evaporation between 60° C. and 100° C. Drying can be performed under ambient pressure or under vacuum, and in the presence of an inert gas such as nitrogen.

The nickel solution, including nickel(II) ions and water, can be prepared by dissolving a nickel(II) salt in water. The nickel salt can be any salt that is soluble in water, for example $NiCl_2$, $NiSO_4$, and $Ni(NO_3)_2$. The precipitant solution, including bicarbonate ions, can be prepared by dissolving a bicarbonate salt, for example, $NaHCO_3$ and $NH_4HCO_3$, in water or prepared in-situ by dissolving $CO_2$ and an alkali metal hydroxide or ammonia in water by known methods. Likewise, the precipitant solution, including carbonate ions, can be prepared by dissolving a carbonate salt, for example $Na_2CO_3$ or prepared in-situ by dissolving $CO_2$ and an alkali metal hydroxide in water by known methods. The anion of the nickel salt and cation of the bicarbonate or carbonate salt can be selected such that a salt produced from the precipitation, including both the cation and anion from the reaction mixture (for example NaCl), is soluble in the water of the reaction mixture. Such a selection provides a method for separating said salt product from the precipitated nickel composition.

Also disclosed is a method of making a nickel-containing solid including nickel metal. The method includes: (i) providing the nickel compositions disclosed above; and (ii) reducing at least a portion of the nickel composition of step (i) with a reducing agent to form a nickel-containing solid, including nickel metal, wherein said nickel-containing solid is adapted to effectively react with a bidendate phosphorus-containing ligand to form a nickel complex of the phosphorus-containing ligand. The nickel-containing solid is more reactive with phosphorus-containing ligands than nickel-containing solids made by other processes, such as INCO type 123 nickel metal powder, or various other Ni(0) compositions made from nickel oxide, nickel formate, nickel oxalate, nickel hydroxide, and nickel carbonate. The high reactivity is believed to be partially due to the BNC processes disclosed above, as well as the reducing process. The reducing agent can be hydrogen, carbon monoxide, methane, ammonia, merely to name a few non-limiting examples of suitable reducing agents.

As previously stated, the amount of bicarbonate or carbonate ions fed relative to the nickel(II) ions charged greatly affects the reactivity of the resulting nickel-containing solid with the phosphorus-containing ligand to make a nickel complex. Because of the high costs of nickel, producers of BNC-type nickel compositions would be led to add excess amounts of the precipitant solution so as to recover as much of the nickel as economically feasible. However, it has been surprisingly found that the use of excess precipitant produces nickel metal of low reactivity for the phosphorus-ligand complex reaction. Highly reactive nickel is produced when reduced levels of precipitant are used, and presumably more of the nickel(II) ions are allowed to remain dissolved in the water of the resulting reaction mixture.

It has also been found that the precipitated nickel composition made using bicarbonate ions filters and washes much faster than the precipitated nickel composition made using carbonate ions. Also, the filtered precipitated nickel composition made using bicarbonate ions dries to a soft powder with little shrinkage. For these reasons, producing the nickel-containing solid using bicarbonate ions provides further desirable properties for downstream processing and handling of the dried precipitated nickel composition.

The reduction of the nickel composition with a reducing agent to form a nickel-containing solid can be performed at a temperature in the range from about 200° C. to about 650° C., including from about 250° C. to about 450° C., and from about 275° C. to about 325° C. The reduction pressure can range from about 0.01 atmospheres to about 100 atmospheres. Reduction can be carried out for a period of at least about 30 minutes using a stoichiometric excess of a reducing agent, such as hydrogen, even though one mole of hydrogen per mole of nickel composition is the theoretical and stoichiometric amount required for reduction. For example, the reducing period can be between about 1 to about 2 hours using a 2:1 mole ratio of hydrogen to nickel composition.

The disclosed nickel containing solids can be reacted with a phosphorus-containing ligand to make a nickel complex of the phosphorus-containing ligand. Such complexes are useful as a catalyst precursor for at least one of the following reactions: (1) reacting 1,3-butadiene with hydrogen cyanide to produce 2-methyl-3-butenenitrile and 3-pentenenitrile; (2) reacting 2-methyl-3-butenenitrile to produce 3-pentenenitrile; (3) reacting 3-pentenenitrile with hydrogen cyanide in the presence of a Lewis acid to produce adiponitrile; and (4) reaction 2-pentenenitrile with hydrogen cyanide in the presence of a Lewis acid to produce 3-pentenenitrile, 4-pentenenitrile, and adiponitrile.

DEFINITIONS OF ABBREVIATIONS

ADN=adiponitrile; Aryl=unsubstituted or substituted aryl radical including 6 to 18 carbon atoms; BD=1,3-butadiene, $C_4H_7C\equiv N$=a pentenenitrile selected from 4PN, 3PN, 2PN, 2M3BN, and 2M2BN isomers, or any combination of such members; hrs=hours; c2PN=cis-2-pentenenitrile; c3PN=cis-3-pentenenitrile; dinitrile or dinitriles=ADN, MGN, and ESN unless specifically limited; ESN=ethylsuccinonitrile; 2M2BN=2-methyl-2-butenenitrile including both (E)-2M2BN and (Z)-2M2BN isomers unless specifically limited; 2M3BN=2-methyl-3-butenenitrile; (E)-2M2BN=(E)-2-methyl-2-butenenitrile; (Z)-2M2BN=(Z)-2-methyl-2-butenenitrile; MGN=2-methylglutaronitrile; pentenenitrile or pentenenitriles=4PN, 3PN, 2PN, 2M3BN, and 2M2BN isomers unless specifically limited; 2PN=2-pentenenitrile including both c2PN and t2PN isomers unless specifically limited; 3PN=3-pentenenitrile including both c3PN and t3PN unless specifically limited; 4PN=4-pentenenitrile; ppm=parts per million by weight unless stated otherwise; t2PN=trans-2-pentenenitrile; t3PN=trans-3-pentenenitrile; VN=valeronitrile; wt %=% by weight.

EXAMPLES

Sources of Nickel

Vale Inco type 123 nickel metal powder (Chemical Abstract Service registry number 7440-02-0) from Vale Inco Limited, Toronto, Ontario, Canada, is produced by thermal decomposition of nickel carbonyl, $Ni(CO)_4$, and is said to have a particle size of 3.5-4.5 μm as measured by a Fisher sub-sieve sizer and a typical specific surface area of about 0.4 $m^2$/gram. This nickel powder is not soluble in the pentenenitrile solvent of the Examples.

A sample of basic nickel(II) carbonate (BNC) was supplied by MetChem Corporation, an American distributor of this material. According to the vendor, the basic nickel(II) carbonate provided is produced by precipitating the basic nickel(II) carbonate from an aqueous solution including nickel(II), ammonia, ammonium carbonate, and water. According to the vendor, the basic nickel(II) carbonate is produced from an ore including nickel and the basic nickel(II) carbonate can optionally further include at least one element selected from the group consisting of aluminum, calcium, cobalt, copper, iron, magnesium, manganese, sodium, sulfur, and zinc. One sample had a chemical analysis shown in Table 1.

TABLE 1

Lab Results for the MetChem Basic Nickel Carbonate Powder.
Nickel 47% by weight

| Cobalt 65 ppm | Copper 20 ppm | Iron 55 ppm | Zinc 12 ppm |
|---|---|---|---|
| Magnesium 60 ppm | Calcium 60 ppm | Sodium 60 ppm | Sulfur 175 ppm |

Suitable basic nickel carbonates can also be produced by precipitating the basic nickel(II) carbonate from an aqueous solution including nickel(II), carbonate anion, and water. Suitable basic nickel carbonates can also be produced by precipitating the basic nickel(II) carbonate from an aqueous solution including nickel(II), bicarbonate anions, and water.

As such, the BNC are nickel compositions including nickel (II) and at least one anion selected from the group consisting of carbonate and hydroxide. But during drying, thermal treatment, and reduction at elevated temperatures, the BNC can partially or fully decompose to lose water, $CO_2$, or both water and $CO_2$ to produce nickel compositions including nickel(II) and at least one anion selected from the group consisting of carbonate, bicarbonate, hydroxide, and oxide.

Suitable nickel compositions of the invention can also be selected from the group consisting of a basic nickel(II) carbonate; nickel(II) hydroxide; nickel(II) oxide; hydrate complexes of basic nickel(II) carbonate, nickel(II) hydroxide, and nickel(II) oxide; and ammonia complexes of basic nickel(II) carbonate, nickel(II) hydroxide, and nickel(II) oxide.

Monodentate Phosphorus-Containing Ligand

Examples 1 and 6 use a monodentate phosphite, TTP, that is derived from the reaction of an m-cresol/p-cresol/phenol mixture with $PCl_3$. TTP is an example of a compound of Formula II.

$$[m\text{-}(CH_3)C_6H_4O]_x[p\text{-}(CH_3)C_6H_4O]_y(C_6H_5O)_zP \qquad \text{TTP}$$

wherein x+y+z=3.

This series of experiments use a recycled ligand as a source of TTP from an ADN manufacturing plant that includes the reaction steps (1) BD hydrocyanation to produce 3PN and 2M3BN, (2) isomerization of 2M3BN to 3PN, and (3) 3PN hydrocyanation to produce ADN with a catalyst including zero-valent nickel and the monodentate TTP ligand that is shared between the three reaction steps above. This recycled ligand was diluted with 3PN to give what will be designated as the "recycle TTP solution" including 80 wt % TTP, 1.16 wt % zero-valent nickel [Ni(0)] as $(TTP)_4Ni$ complex, a mixture of valeronitrile and pentenenitriles including 2PN, 3PN, 4PN, 2M3BN, and 2M2BN isomers, and dinitriles including ADN, MGN, and ESN.

In all of the Examples 1-6, the listed reactants were added to a 100 mL glass reactor in a dry box to limit contact with oxygen then each reaction was carried out in a laboratory fume hood at 90° C. with magnetic stirring (1000 rpm) of the reaction mixture under a nitrogen atmosphere. Filtered liquid samples were withdrawn from the reactor at the described intervals and analyzed for the soluble Ni(0) content.

Example 1 (Comparative)

To avoid contact with air, a reactor bottle, equipped with a magnetic stir bar, is charged with reactants inside a Vacuum Atmospheres dry box operating with a dry nitrogen atmosphere. To this bottle are added 100 gm of the recycle TTP solution and 5.0 gm of Vale Inco type 123 nickel metal powder. The reactor bottle was sealed, removed from the dry box, and moved to a laboratory fume hood where it is placed on a magnetic stir plate. The reaction mixture within the reaction bottle is then quickly heated to 80° C. Filtered liquid samples from the reaction mixture are removed from the reactor bottle at different time intervals and the measured soluble Ni(0) content of withdrawn samples using liquid chromatography (LC) is provided in the Example 1 column of Table 2.

The absence of an observable reaction between TTP and the nickel powder to form soluble Ni(0) complexes of TTP, for example $(TTP)_4Ni$, is attributed to no halogenated catalyst being present in the recycle TTP solution.

According to U.S. Pat. Nos. 3,903,120 and 4,416,825, suitable halogenated catalysts for this reaction to form nickel complexes of the ligand include compounds of the formula $(R'O)_xR''_yPX$ where R' and R'' are alkyl or aryl radicals having up to 18 carbon atoms, being either the same or different, x and z are 1-2, y is 0 or 1, and the sum of x, y and z equals 3 and wherein X is a halide selected from the group consisting of chloride, bromide and iodide. Such compounds are also said to be prepared in situ by reaction of an appropriate ligand having at least two ROP linkages (R is an alkyl or aryl radical having up to 18 carbon atoms, O is a oxygen atom, P is a phosphorus atom) with a suitable halide source as an initiator such as a halide or alkyl-substituted halide of phosphorus, arsenic or antimony such as $CH_3PCl_2$, $CH_3AsCl_2$ or $CH_3SbCl_2$; an appropriate metal halide; elemental halogen such as chlorine bromine or iodine; or the corresponding hydrogen halide or thionyl halide. Suitable metal halides for this purpose include those of Cr, Ni, Ti, Cu, Co, Fe, Hg, Sn, Li, K, Ca, Ba, Sc, Ce, V, Mn, Be, Ru, Rh, Pd, Zn, Cd, Al, Th, Zr, and Hf. The halide can be chloride, bromide or iodide. Particularly suitable halide sources include $PX_3$, $TiX_4$, $ZrX_4$, $HfX_4$ and HX wherein X is chloride, bromide, or iodide. Mixtures of two or more of the initiators or halogenated catalyst can be used in carrying out the reaction to form the nickel complexes.

Example 2 (Comparative)

This Example is identical to Example 1, except that 20 microliters of $PCl_3$ is also charged to the 100 mL glass reactor (245 ppm Cl) in the dry box and the measured soluble Ni(0) content of withdrawn samples is provided in the Example 2 column of Table 2. In comparison to Example 1, Example 2 shows that the Vale Inco type 123 nickel metal powder reacts with the monodentate TTP ligand upon the introduction of the $PCl_3$ to the reaction mixture.

Example 3

Twenty five grams of the MetChem BNC is charged into a glass reduction tube then hydrogen is flowed at 0.5 liter/minute and 1 atmosphere over this material at 400° C. for 16 hours. Heat is supplied to the external wall of the reduction tube using a temperature-controlled tube furnace and the internal temperature is measured with a thermocouple. The reduction tube is sealed, taken into the dry box, and then the powdery, nickel-containing solid inside the reduction tube is transferred into a bottle. The solid was magnetic, indicating that nickel metal is produced by the reduction. Like the Vale Inco type 123 nickel metal powder, the nickel metal from the reduction of BNC is not soluble in the pentenenitrile solvent of the Examples.

A measured surface area of the nickel metal is between 0.5 to 2.5 square meters per gram of nickel metal. From other BNC samples, a measured surface area of the nickel metal is up to 30 square meters per gram of nickel metal. In some cases, the reactivity of the nickel metal with the phosphorus-containing ligands can be higher as the surface area of the nickel metal increases.

The preparation of the nickel metal is repeated further including pre-heating the BNC nickel composition between 150° C. to 700° C., for example at a temperature between 200° C. to 600° C., for a period of time between 0.01 to 24 hours to produce a pre-heated material prior to flowing hydrogen at 0.5 liter/minute and 1 atmosphere over this pre-heated material at 400° C. for 16 hours. For example, air or nitrogen gas flows over the BNC nickel composition at a temperature between 200° C. to 600° C., then hydrogen gas flows at 0.5 liter/minute and 1 atmosphere over this pre-heated material at 250° C. to 350° C. for 0.16 to 12 hours.

The 100 mL glass reactor is charged with 100 gm of the recycle TTP solution and 5.0 gm of the nickel metal in a dry box and the measured soluble Ni(0) content of withdrawn samples is provided in the Example 3 column of Table 2. Hence, this Example is identical to Example 1, except for the different source of nickel metal. In comparison to Example 1, this Example shows that the nickel metal from the reduction of BNC reacts with the monodentate TIP ligand without a halogenated catalyst of U.S. Pat. Nos. 3,903,120 and 4,416,825 being present in the reaction mixture.

Example 4

This Example is identical to Example 3, except that 20 microliters of $PCl_3$ is also charged to the 100 mL glass reactor in the dry box (245 ppm Cl) and the measured soluble Ni(0) content of withdrawn samples is provided in the Example 4 column of Table 2.

Like the Vale Inco type 123 nickel metal powder (Example 2), this Example shows that the $PCl_3$ addition also accelerates the reaction between the nickel metal from the reduction of BNC and the monodentate TTP ligand.

But in comparison to Example 2, this Example shows that the nickel metal from the reduction of BNC reacts faster with the monodentate TTP ligand when the same amount of $PCl_3$ is charged to the reaction mixture.

TABLE 2

Data for Examples 1 through 4.

| Sample Time (Hours) | Example | | | |
|---|---|---|---|---|
| | 1 | 2 | 3 | 4 |
| 0 | 1.16 wt % | 1.16 wt % | 1.16 wt % | 1.16 wt % |
| 2 | 1.14 wt % | 1.26 wt % | 1.16 wt % | 2.53 wt % |
| 4 | 1.12 wt % | 1.59 wt % | 1.23 wt % | 3.06 wt % |
| 6 | 1.10 wt % | 1.97 wt % | 1.29 wt % | 2.92 wt % |
| 8 | 1.12 wt % | 2.24 wt % | 1.27 wt % | 2.86 wt % |
| 24 | 1.13 wt % | 3.03 wt % | 1.40 wt % | 3.03 wt % |

Example 4 is repeated to form nickel complexes of TTP further including charging to the 100 mL glass reactor at least halogenated catalyst including a phosphorus-halide bond selected from the group consisting of $R^{17}PCl_2$, $R^{18}OPCl_2$, $[R^{19}][R^{20}]PCl$, $[R^{21}][R^{22}O]PCl$, and $[R^{23}O][R^{24}O]PCl$; wherein $R^{17}$, $R^{18}$, $R^{19}$, $R^{20}$, $R^{21}$, $R^{22}$, $R^{23}$, and $R^{24}$ are independently selected from the group consisting of $C_1$ to $C_{18}$ hydrocarbyl radicals.

Example 4 is repeated to form nickel complexes of TTP further including adjusting a second molar ratio between 5 and 1000. The adjusting involves charging to the 100 mL glass reactor between 5 and 1000 total moles of the at least one halogenated catalyst including a phosphorus-halide bond per million total moles of the at least one monodentate phosphorus-containing ligand.

Example 5 (Comparison)

Example 1 is repeated except that 0.047 gm of zinc chloride ($ZnCl_2$) is also charged to the reactor in the dry box prior to heating to 90° C. in the laboratory fume hood. This $ZnCl_2$ charge corresponds to 245 ppm Cl in the reactor, the same Cl concentration as provided by the $PCl_3$ charge in Example 2. In this example, no increase in the soluble Ni(0) concentration was observed over a reaction period of 24 hours. This Example follows from U.S. Pat. No. 3,903,120 but in this case no reaction occurred. The reason for this discrepancy is believed to be that the TTP ligand used in the $ZnCl_2$ experiments of U.S. Pat. No. 3,903,120 also contained an organochlorodite of the formula $(R'O)_xR''_yPX$, which was the halogenated catalyst for the reaction to form nickel complexes rather than the added metal halide salt ($ZnCl_2$).

Example 6

Embodiment of the Method Provided by the Present Invention

Example 3 is repeated except that 0.047 gm of $ZnCl_2$ is also charged to the reactor (245 ppm Cl) in the dry box prior to heating to 90° C. in the laboratory fume hood. The Ni(0) concentration of the reactor contents in weight % is shown as a function of time in Table 2 below:

|  | Time (hrs) | | | | | |
| --- | --- | --- | --- | --- | --- | --- |
|  | 0 | 2 | 4 | 6 | 8 | 24 |
| Total Soluble Nickel (wt %) | 1.16 | 1.53 | 1.64 | 1.86 | 1.93 | 2.58 |

In the presence of $ZnCl_2$, the results of Examples 5 and 6 shows the much higher reactivity of the nickel metal derived from reducing BNC compared to the Vale Inco type 123 nickel metal powder.

Examples 1-6 demonstrate that the nickel metal from BNC is much more reactive with the monodentate TTP ligand than the Vale Inco type 123 nickel metal powder that is derived from $Ni(CO)_4$ thermal decomposition.

Bidentate Phosphorus-Containing Ligand

Examples 7 through 12 and 14 through 16 use a bidentate phosphite ligand, Ligand A. Ligand A can be prepared by any suitable synthetic means known in the art. For example, 3,3'-diisopropyl-5,5',6,6'-tetramethyl-2,2'-biphenol can be prepared by the procedure disclosed in U.S. Published Patent Application No. 2003/0100802 in which 4-methylthymol can undergo oxidative coupling to the substituted biphenol in the presence of a copper chlorohydroxide-TMEDA complex (TMEDA is N,N,N',N'-tetramethylethylenediamine) and air. The phosphorochloridite of 2,4-xylenol, $[(CH_3)_2C_6H_3O]_2PCl$, can be prepared, for example, by the procedure disclosed in U.S. Published Patent Application No. 2004/0106815. To selectively form this phosphorochloridite, anhydrous triethylamine and 2,4-xylenol can be added separately and concurrently in a controlled manner to $PCl_3$ dissolved in an appropriate solvent under temperature-controlled conditions. The reaction of this phosphorochloridite with the 3,3'-diisopropyl-5,5',6,6'-tetramethyl-2,2'-biphenol to form the desired Ligand A can be performed, for example, according to the method disclosed in U.S. Pat. No. 6,069,267. The phosphorochloridite can be reacted with 3,3'-diisopropyl-5,5',6,6'-tetramethyl-2,2'-biphenol in the presence of an organic base to form Ligand A, which can be isolated according to techniques well known in the art, for example as also described in U.S. Pat. No. 6,069,267. Ligand A is an example of a compound of Formula I and the Ligand A solutions in 3PN solvent below do not contain any halogenated catalysts of U.S. Pat. No. 3,903,120.

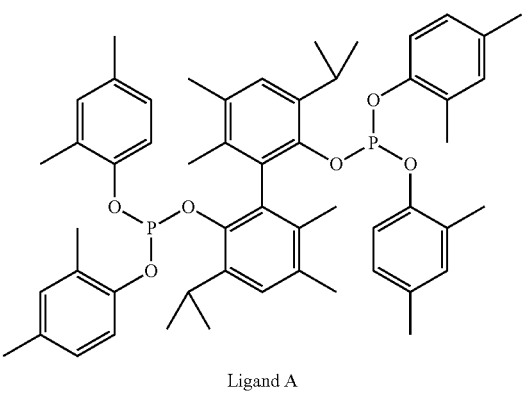

Ligand A

Example 7 (Comparative)

To avoid contact with air, a reactor bottle, equipped with a magnetic stir bar, is charged with reactants inside a Vacuum Atmospheres dry box operating with a dry nitrogen atmosphere. To this bottle is added 80 gm of a 10% by weight Ligand A solution in 3PN solvent, 3.2 gm of Vale Inco type 123 nickel metal powder, and 1.0 gm of anhydrous $ZnCl_2$. The reactor bottle is sealed, removed from the dry box, and moved to a laboratory fume hood where it is placed on a magnetic stir plate. The reaction mixture within the reaction bottle is then heated to 80° C. Filtered liquid samples from the reaction mixture are removed from the reactor bottle at intervals of one hour, with a final sample being taken after 24 hours. The amount of soluble nickel in the 24 hour sample is measured using LC, and no soluble nickel was detected. This result indicates that the reaction produced less than about 20-50 ppm soluble nickel in the form of soluble nickel complexes of Ligand A.

Example 8 (Comparative)

Example 7 is repeated except that the reaction bottle is charged with 80 gm of 5% by weight Ligand A solution in 3PN solvent, 3.2 gm of Vale Inco type 123 nickel metal powder, 0.5 gm of $ZnCl_2$, and 15 microliters of $PCl_3$. A calibrated absorption method that detects the divalent nickel complex (Ligand A)Ni($\eta^3$-$C_4H_7$)C≡N—$ZnCl_2$ by the amount of absorption at a wavelength of 380 nanometers is used. This absorption method is calibrated against a LC analysis for total soluble nickel. The data below indicates a rate of only about 11 ppm soluble nickel/hour over the 72 hour reaction period.

|  | Time (hrs) | | | | | |
| --- | --- | --- | --- | --- | --- | --- |
|  | 2 | 4 | 6 | 8 | 24 | 72 |
| Total Soluble Nickel (ppm) | 0 | 0 | 120 | 147 | 397 | 856 |

Example 9

MetChem BNC is reduced with hydrogen to produce a nickel-containing solid including nickel metal similar to what is described in Example 3 except that 50 gm of BNC is charged into the glass reduction tube then hydrogen gas is flowed at 0.5 liter/minute over this material at 400° C. for a shorter period of 4 hours.

A measured surface area of the nickel metal is between 0.5 to 2.5 square meters per gram of nickel metal.

The preparation of the nickel metal is repeated further including pre-heating the BNC nickel composition between 150° C. to 400° C. to produce a pre-heated material prior to flowing hydrogen at 0.5 liter/minute and 1 atmosphere over this pre-heated material at 400° C. for 16 hours. For example, nitrogen flows over the BNC nickel composition for a period of time between 150° C. to 400° C. by flowing nitrogen over the BNC nickel composition then hydrogen flows at 0.5 liter/minute and 1 atmosphere over this pre-heated material at 400° C. for 16 hours.

Two experiments similar to that described in Example 7 were performed. In both separate experiments, each reaction bottle is charged with 80 gm of a 5% by weight of Ligand A solution in 3PN solvent, 3.2 gm of the nickel metal of this Example, and 0.5 gm of anhydrous $ZnCl_2$. After the reaction mixture inside the reactor bottle is then heated to 80° C., filtered liquid samples are withdrawn as a function of time like that described in Example 7. Analysis of the samples by LC for soluble nickel content of each sample gives the following results.

TABLE 3

Example 9 Results.

| Time (hours) | Measured Total Soluble Nickel (ppm) | |
|---|---|---|
| | First Experiment | Second Experiment |
| 0 | 0 | 0 |
| 1 | 942 | 851 |
| 2 | 1460 | 1291 |
| 3 | 1685 | 1607 |
| 4 | 1846 | 1729 |
| 5 | 1851 | 1898 |
| 6 | 1952 | 1952 |
| 7 | 2042 | 2010 |
| 24 | 2226 | 2306 |

The nickel metal from the reduction of BNC reacted with the Ligand A in the presence of $ZnCl_2$ to form soluble nickel complexes of Ligand A, including the divalent nickel complex (LigandA)Ni($\eta^3$-$C_4H_7$)C≡N—$ZnCl_2$. The LC analysis also showed no Ligand A degradation during the course of this reaction.

Even in the absence of the $PCl_3$ charge, the initial reaction rate of 1040 ppm total soluble nickel/hour with the nickel metal from BNC is approximately 100 times faster than that obtained with the Vale Inco type 123 nickel metal powder in Example 8.

The reacting of the Ligand A solution with a nickel metal of Example 9 is repeated to form nickel complexes of Ligand A while applying ultra-sonic energy to the reaction mixture.

Example 10

This example is identical to Example 9, except that 15 microliters of $PCl_3$ is also charged to the reaction bottle at the beginning of the reaction.

| | Time (hrs) | | | | | | | |
|---|---|---|---|---|---|---|---|---|
| | 1 | 2 | 3 | 4 | 5 | 6 | 7 | 24 |
| Total Soluble Nickel (ppm) | 927 | 1242 | 1465 | 1575 | 1670 | 1685 | 1746 | 1856 |

In comparison to Example 9, these data show an initial reaction rate to form soluble nickel complexes was slightly faster but the addition of $PCl_3$ to the reaction mixture did not increase the total soluble nickel concentration at the 24 hour period.

Example 11 (Comparative)

This example is identical to Example 9, except that no $ZnCl_2$ is charged to the reactor. LC analysis of a filtered liquid sample taken from the reaction mixture after 24 hours shows only 23 ppm total soluble nickel to be present. This example indicates that a Lewis acid, like $ZnCl_2$, provides higher levels of total soluble nickel even when using the reactive nickel of this invention.

Example 9 is repeated to form nickel complexes of Ligand A wherein the at least one Lewis acid is selected from the group consisting of inorganic or organometallic compound in which the cation is selected from the group including scandium, titanium, vanadium, chromium, manganese, iron, cobalt, copper, zinc, boron, aluminum, yttrium, zirconium, niobium, molybdenum, cadmium, rhenium, lanthanum, europium, ytterbium, tantalum, samarium, and tin. For example, Example 9 is repeated with $FeCl_2$ or a combination of $ZnCl_2$ and $FeCl_2$.

Example 9 is repeated to form nickel complexes of Ligand A further including adjusting a first molar ratio between 0.5 and 2.5. The adjusting involves charging to the reactor bottle between 0.5 and 2.5 total moles of the at least one Lewis acid per total mole of at least one bidentate phosphorus-containing ligand.

Example 4 is repeated to form nickel complexes of TTP further including adjusting a second molar ratio between 5 and 1000. The adjusting involves charging to the 100 mL glass reactor between 5 and 1000 moles of the halogenated catalyst including a phosphorus-halide bond per million moles of the at least one monodentate phosphorus-containing ligand.

Example 12

Embodiment of the Method Provided by the Present Invention

Example 9 is repeated wherein the Ligand A solution in 3PN solvent further includes monodentate phosphite ligands of the following formulae.

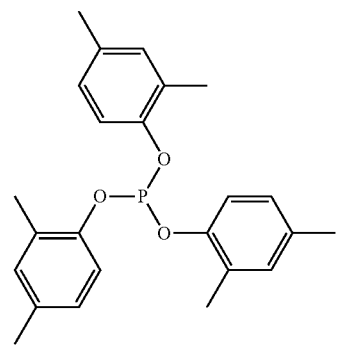

Ligand B

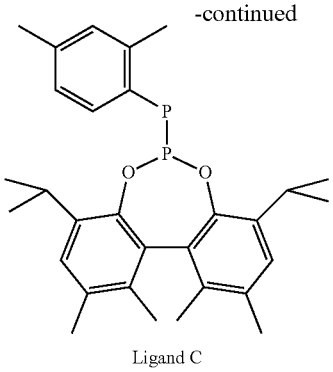

Ligand C

This Ligand A solution in 3PN solvent, including Ligand A, B, and C does not contain any halogenated catalysts of U.S. Pat. No. 3,903,120. The concentrations of Ligand B and Ligand C were each between 0.01% and 3% by weight of the Ligand A solution in 3PN solvent. The reaction performance with the nickel metal from BNC was identical to the experiments of Example 9 to form nickel complexes including (Ligand A)Ni($\eta^3$-$C_4H_7$)C≡N—$ZnCl_2$.

Example 13

To form nickel complexes of other monodentate phosphorus-containing ligands, Examples 3, 4, and 6 are repeated wherein a ligand of Formula II replaces the TTP ligand of the recycle TTP solution.

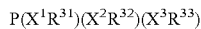
$$P(X^1R^{31})(X^2R^{32})(X^3R^{33}) \quad \text{Formula II}$$

wherein, $X^1$, $X^2$, $X^3$ independently represent oxygen or a single bond, and $R^{31}$, $R^{32}$, $R^{33}$ independently represent identical or different, single or bridged organic radicals.

The at least one monodentate phosphorus-containing ligand of Formula II is selected from the group consisting of a monodentate phosphite, a monodentate phosphonite, a monodentate phosphinite, and a monodentate phosphine.

To form nickel complexes of other bidentate phosphorus-containing ligands, Examples 9, 10, and 12 are repeated wherein a ligand of Formula I replaces Ligand A.

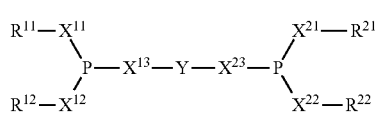

Formula I wherein, $X^{11}$, $X^{12}$, $X^{13}$, $X^{21}$, $X^{22}$, $X^{23}$ independently represent oxygen or a single bond;

$R^{11}$, $R^{12}$ independently represent identical or different, single or bridged organic radicals;

$R^{21}$, $R^{22}$ independently represent identical or different, single or bridged organic radicals; and Y represents a bridging group.

The at least one bidentate phosphorus-containing ligand of Formula I is selected from the group consisting of a bidentate phosphite, a bidentate phosphonite, a bidentate phosphinite, a bidentate phosphine, and a mixed bidentate ligand; wherein the mixed bidentate ligand is selected from the group consisting of a phosphite-phosphonite, a phosphite-phosphinite, a phosphite-phosphine, a phosphonite-phosphinite, a phosphonite-phosphine, and a phosphinite-phosphine.

The at least one bidentate phosphorus-containing ligand is selected from the group consisting of Formula IIIa, Formula IIIb, Formula IIIc, or any combinations of such members,

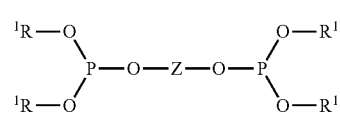

Formula IIIa

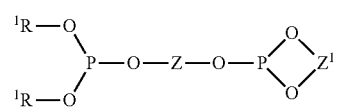

Formula IIIb

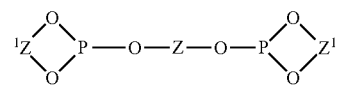

Formula IIIc wherein in Formulae IIIa, IIIb, and IIIc, $R^1$ is phenyl, unsubstituted or substituted with one or more $C_1$ to $C_{12}$ alkyl, $C_1$ to $C_{12}$ alkoxy groups, or groups of Formulae A and B, or —$(CH_2)_nOY^2$; or naphthyl, unsubstituted or substituted with one or more $C_1$ to $C_{12}$ alkyl or $C_1$ to $C_{12}$ alkoxy groups, or groups of Formulae A and B, or —$(CH_2)_nOY^2$; or 5,6,7,8-tetrahydro-1-naphthyl;

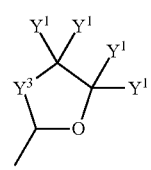

Formula A

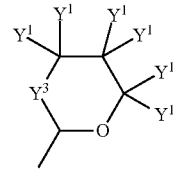

Formula B wherein in Formulae A and B, $Y^1$ is independently selected from the group of H, $C_1$ to $C_{18}$ alkyl, cycloalkyl, or aryl, $Y^2$ is independently selected from the group of $C_1$ to $C_{18}$ alkyl, cycloalkyl, or aryl, $Y^3$ is independently selected from the group of O or $CH_2$, and n=1 to 4;

wherein in Formulae IIIa, IIIb, and IIIc,

O—Z—O and O—$Z^1$—O are independently selected from the group consisting of structural Formulae IV, V, VI, VII, and VIII:

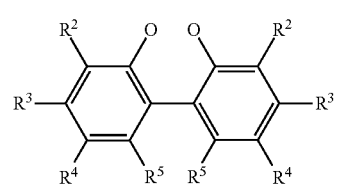

IV

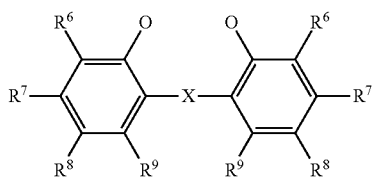

V wherein in Formulae IV and V, $R^2$, $R^3$, $R^4$, $R^5$, $R^6$, $R^7$, $R^8$, and $R^9$ are independently selected from the group consisting of H, $C_1$ to $C_{12}$ alkyl, and $C_1$ to $C_{12}$ alkoxy; X is O, S, or CH($R^{10}$);

$R^{10}$ is H or $C_1$ to $C_{12}$ alkyl;

VI

VII wherein in Formulae VI and VII, $R^{20}$ and $R^{30}$ are independently selected from the group consisting of H, $C_1$ to $C_{12}$ alkyl, and $C_1$ to $C_{12}$ alkoxy, and $CO_2R^{13}$;

$R^{13}$ is $C_1$ to $C_{12}$ alkyl or $C_6$ to $C_{10}$ aryl, unsubstituted or substituted with $C_1$ to $C_4$ alkyl;

W is O, S, or CH($R^{14}$);

$R^{14}$ is H or $C_1$ to $C_{12}$ alkyl;

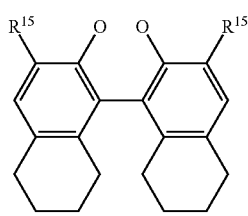

VIII and wherein in Formulae VIII, $R^{15}$ is selected from the group consisting of H, $C_1$ to $C_{12}$ alkyl, and $C_1$ to $C_{12}$ alkoxy and $CO_2R^{16}$;

$R^{16}$ is $C_1$ to $C_{12}$ alkyl or $C_6$ to $C_{10}$ aryl, unsubstituted or substituted with $C_1$ to $C_4$ alkyl.

To form nickel complexes of monodentate and bidentate phosphorus-containing ligands, respectively, Examples 4 and 9 are repeated with nickel metals from the reduction of nickel compositions including nickel(II) and at least one anion selected from the group consisting of oxalate, a $C_1$ to $C_6$ carboxylate, hydroxide, and oxide.

Example 14

A black nickel(II) oxide from the J. T. Baker chemical company (number 2792) is reduced with hydrogen at 300° C. for a period of 16 hrs using a hydrogen flow rate of 0.2 liters/minute. After reduction, the resulting nickel-containing solid is black and magnetic indicating the presence of nickel metal.

Under a nitrogen atmosphere, a reactor bottle is charged with 80 gm of a 5% by weight Ligand A solution in 3PN solvent, 3.2 gm of the nickel metal of this Example, and 0.5 gm of anhydrous $ZnCl_2$. After the reaction mixture inside the reactor bottle is heated to 80° C., filtered liquid samples are withdrawn as a function of time and analyzed for soluble nickel concentration, and the following results were obtained.

| | Time (hrs) | | | | | | | |
|---|---|---|---|---|---|---|---|---|
| | 0 | 1 | 2 | 3 | 4 | 5 | 6 | 7 | 24 |
| Total Soluble Nickel (ppm) | 0 | 99 | 210 | 245 | 305 | 355 | 402 | 481 | 919 |

Example 15

A nickel(II) hydroxide from the Research Inorganics Chemical company is reduced with hydrogen at 300° C. for a period of 16 hrs using a hydrogen flow rate of 0.2 liters/minute. After reduction, the resulting the nickel-containing solids were black and magnetic indicating the presence of nickel metal.

Under a nitrogen atmosphere, a reactor bottle is charged with 80 gm of a 5% by weight Ligand A solution in 3PN solvent, 3.2 gm of the nickel metal of this Example, and 0.5 gm of anhydrous $ZnCl_2$. After the reaction mixture inside the reactor bottle is heated to 80° C., filtered liquid samples are withdrawn as a function of time and analyzed for soluble nickel concentration, and the following results were obtained.

| | Time (hrs) | | | | | | |
|---|---|---|---|---|---|---|---|
| | 0 | 1 | 2 | 3 | 4 | 5 | 6 | 7 |
| Total Soluble Nickel (ppm) | 0 | 1221 | 1561 | 1707 | 1793 | 1837 | 1875 | 1883 |

Example 16

A nickel(II) carbonate having the stated chemical formula $NiCO_3$ and a measured nickel content of 46.9% from the J. T. Baker chemical company (number 2764) is reduced with hydrogen at 300° C. for a period of 16 hrs using a hydrogen flow rate of 0.2 liters/minute. After reduction, the resulting the nickel-containing solids were black and magnetic indicating the presence of nickel metal.

Under a nitrogen atmosphere, a reactor bottle is charged with 80 gm of a 5% by weight Ligand A solution in 3PN solvent, 3.2 gm of the nickel metal of this Example, and 0.5 gm of anhydrous $ZnCl_2$. After the reaction mixture inside the reactor bottle is heated to 80° C., filtered liquid samples are withdrawn as a function of time and analyzed for soluble nickel concentration, and the following results were obtained.

|                              | Time (hrs) |   |     |     |     |     |     |     |     |
| ---------------------------- | ---------- | - | --- | --- | --- | --- | --- | --- | --- |
|                              | 0          | 1 | 2   | 3   | 4   | 5   | 6   | 7   | 24  |
| Total Soluble Nickel (ppm)   | 0          | 0 | 110 | 141 | 192 | 223 | 283 | 309 | 735 |

Example 17

3PN Hydrocyanation with Nickel Complexes

In the presence of a Lewis acid promoter, like $ZnCl_2$, triphenylboron, or compounds of the chemical formula [Ni$(C_4H_7C\equiv N)_6$][$(C_6H_5)_3BC\equiv NB(C_6H_5)_3$]$_2$ as disclosed in U.S. Pat. No. 4,749,801, soluble nickel complex of TTP from the reactors of Examples 3, 4, or 6 contacts HC≡N and 3PN in a reaction zone. A catalyst forms converting 3PN to dinitriles including ADN, MGN, and ESN, wherein ADN is the major dinitrile product.

In the presence of a Lewis acid promoter, like $ZnCl_2$, triphenylboron, or compounds of the chemical formula [Ni$(C_4H_7C\equiv N)_6$][$(C_6H_5)_3BC\equiv NB(C_6H_5)_3$]$_2$ as disclosed in U.S. Pat. No. 4,749,801, soluble nickel complex of a monodentate phosphorus-containing compound of Formula II from a reactor of Example 13 contacts HC≡N and 3PN in a reaction zone. A catalyst forms converting 3PN to dinitriles including ADN, MGN, and ESN.

In the presence of a Lewis acid promoter, like $ZnCl_2$, the soluble nickel complexes of Ligand A from the reaction bottles of Example 9, 10, 12, 14, 15, or 16 contacts HC≡N and 3PN in a reaction zone. A catalyst forms converting greater than 90% of the 3PN to dinitriles including ADN, MGN, and ESN, with an ADN distribution of 95-96%. The ADN distribution equals 100%*wt % ADN/(wt % ADN+wt % MGN+wt % ESN), as determined by gas chromatography (GC).

A divalent nickel complex of the form (Ligand A)Ni($\eta^3$-$C_4H_7$)C≡N—$ZnCl_2$ can be in equilibrium with a divalent nickel complex of the form (Ligand A)Ni($\eta^3$-$C_4H_7C\equiv N$) and a zerovalent nickel complex of the form (Ligand A)Ni ($\eta^2$-$C_4H_7C\equiv N$).

In the presence of a Lewis acid promoter, like $ZnCl_2$, the soluble nickel complex of a bidentate phosphorus-containing compound of Formula I from a reaction bottle of Example 13 contacts HC≡N and 3PN in a reaction zone. A catalyst forms converting 3PN to dinitriles including ADN, MGN, and ESN.

Example 18

BD Hydrocyanation with Nickel Complexes

A nickel complex from a reaction mixture of a reactor of Examples 3, 4, 6, 9, 10, 12, 13, 14, 15, or 16 contacts 1,3-butadiene and hydrogen cyanide in a reaction zone. A catalyst forms to produce 3-pentenenitrile, 2-methyl-3-butenenitrile, or a combination thereof.

Example 19

2M3BN Isomerization with Nickel Complexes

A nickel complex from a reaction mixture of a reactor of Examples 3, 4, 6, 9, 10, 12, 13, 14, 15, or 16 contacts 2-methyl-3-butenenitrile in a reaction zone. A catalyst forms converting at least a portion of the 2-methyl-3-butenenitrile to 3-pentenenitrile.

What is claimed is:

1. A method of preparing a nickel complex comprising nickel and at least one phosphorus-containing ligand, comprising:
   (i) providing a nickel composition comprising basic nickel carbonate comprising
      forming a precipitant solution comprising dissolving in water (1) a bicarbonate salt, or (2) a bicarbonate salt and a carbonate salt,
      contacting the precipitant solution with a nickel solution in a precipitation reactor to form a reaction mixture, wherein a mole ratio of bicarbonate ions to nickel ions in the reaction mixture is 0.5:1 to 2:1 and a mole ratio of carbonate ions, if present, to nickel ions in the reaction mixture is 0.5:1 to 1.6:1, and
      precipitating the nickel composition from the reaction mixture;
   (ii) reducing at least a portion of the nickel composition of (i) to form a nickel metal;
   (iii) charging the nickel metal and at least one phosphorus-containing ligand to a first reaction zone; and
   (iv) within the first reaction zone of (a), reacting at least a portion of the nickel metal with the at least one phosphorus-containing ligand to form a reaction mixture including the nickel complex comprising nickel and the at least one phosphorus-containing ligand.

2. The method of claim 1, further comprising charging in (iii) at least one Lewis acid to the first reaction zone.

3. The method of claim 1, further comprising charging in (iii) a solvent comprising a pentenenitrile to the first reaction zone.

4. The method of claim 3 wherein the solvent comprises one or more members of the group consisting of 2-pentenenitrile, 3-pentenenitrile, 4-pentenenitrile, 2-methyl-3-butenenitrile, and 2-methyl-2-butenenitrile.

5. The method of claim 1, wherein the nickel composition of (i) further comprises at least one anion selected from the group consisting of carbonate, oxalate, $C_1$ to $C_6$ carboxylate, hydroxide, and oxide.

6. The method of claim 1, wherein the nickel composition of (i) is selected from the group consisting of a basic nickel(II) carbonate; hydrate complexes of basic nickel(II) carbonate; and ammonia complexes of basic nickel(II) carbonate.

7. The method of claim 1 further comprising precipitating the basic nickel carbonate from at least one aqueous solution selected from the group consisting of (1) an aqueous solution comprising nickel(II), ammonia, ammonium carbonate, and water; (2) an aqueous solution comprising nickel(II), carbonate anion, and water; and (3) an aqueous solution comprising nickel(II), bicarbonate anion, and water.

8. The method of claim 1, further comprising producing the basic nickel carbonate from an ore comprising nickel; and the basic nickel carbonate optionally comprises at least one element selected from the group consisting of aluminum, calcium, cobalt, copper, iron, magnesium, manganese, sodium, sulfur, and zinc.

9. The method of claim 1 wherein the at least one phosphorus-containing ligand is a bidentate phosphorus-containing ligand selected from the group consisting of a bidentate phosphite, a bidentate phosphonite, a bidentate phosphinite, a bidentate phosphine, and a mixed bidentate ligand; wherein the mixed bidentate ligand is selected from the group consisting of a phosphite-phosphonite, a phosphite-phosphinite, a phosphite-phosphine, a phosphonite-phosphinite, a phosphonite-phosphine, and a phosphinite-phosphine.

10. The method of claim 1 wherein the at least one phosphorus-containing ligand is a bidentate phosphorus-containing ligand selected from the group consisting of Formula IIIa, Formula IIIb, Formula IIIc, or combinations thereof,

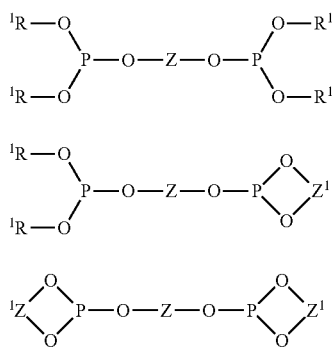
Formula IIIa

Formula IIIb
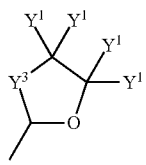

Formula IIIc
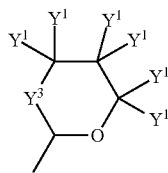

wherein in Formulae IIIa, IIIb, and IIIc,
$R^1$ is phenyl, unsubstituted or substituted with one or more $C_1$ to $C_{12}$ alkyl, $C_1$ to $C_{12}$ alkoxy groups, or groups of Formulae A and B, or $-(CH_2)_nOY^2$; or naphthyl, unsubstituted or substituted with one or more $C_1$ to $C_{12}$ alkyl or $C_1$ to $C_{12}$ alkoxy groups, or groups of Formulae A and B, or $-(CH_2)_nOY^2$; or 5,6,7,8-tetrahydro-1-naphthyl;

Formula A

Formula B wherein in Formulae A and B,
$Y^1$ is independently selected from the group of H, $C_1$ to $C_{18}$ alkyl, cycloalkyl, or aryl, $Y^2$ is independently selected from the group of $C_1$ to $C_{18}$ alkyl, cycloalkyl, or aryl, $Y^3$ is independently selected from the group of O or $CH_2$, and n=1 to 4;

wherein in Formulae IIIa, IIIb, and IIIc,
O—Z—O and O—$Z^1$—O are independently selected from the group consisting of structural Formulae IV, V, VI, VII, and VIII:

IV
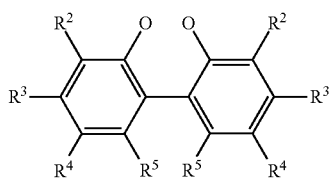

V
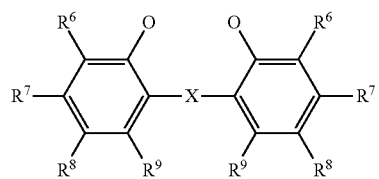

wherein in Formulae IV and V,
$R^2$, $R^3$, $R^4$, $R^5$, $R^6$, $R^7$, $R^8$, and $R^9$ are independently selected from the group consisting of H, $C_1$ to $C_{12}$ alkyl, and $C_1$ to $C_{12}$ alkoxy; X is O, S, or $CH(R^{10})$; $R^{10}$ is H or $C_1$ to $C_{12}$ alkyl;

VI
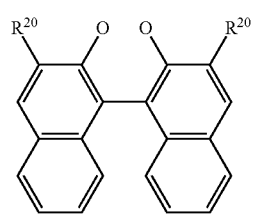

VII
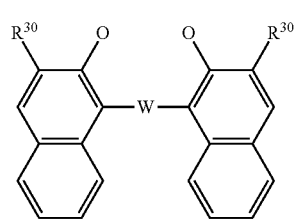

wherein in Formulae VI and VII,
$R^{20}$ and $R^{30}$ are independently selected from the group consisting of H, $C_1$ to $C_{12}$ alkyl, and $C_1$ to $C_{12}$ alkoxy, and $CO_2R^{13}$;
$R^{13}$ is $C_1$ to $C_{12}$ alkyl or $C_6$ to $C_{10}$ aryl, unsubstituted or substituted with $C_1$ to $C_4$ alkyl; W is O, S, or $CH(R^{14})$;
$R^{14}$ is H or $C_1$ to $C_{12}$ alkyl;

VIII
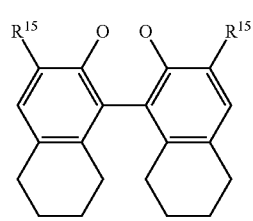

and wherein in Formulae VIII,
$R^{15}$ is selected from the group consisting of H, $C_1$ to $C_{12}$ alkyl, and $C_1$ to $C_{12}$ alkoxy and $CO_2R^{16}$;
$R^{16}$ is $C_1$ to $C_{12}$ alkyl or $C_6$ to $C_{10}$ aryl, unsubstituted or substituted with $C_1$ to $C_4$ alkyl.

11. The method of claim 1 wherein the at least one phosphorus-containing ligand is a bidentate phosphorus-containing ligand, further comprising charging in (iii) at least one monodentate phosphorus-containing ligand selected from the group consisting of a monodentate phosphite, a monodentate phosphonite, a monodentate phosphinite, and a monodentate phosphine.

12. The method of claim 2, wherein the at least one phosphorus-containing ligand in (iii) is a bidentate phosphorus-containing ligand, further comprising adjusting a first molar ratio between about 0.5 and about 2.5, wherein the first molar ratio is defined as total moles of the at least one Lewis acid charged in (iii) divided by total moles of the at least one bidentate phosphorus-containing ligand charged in (iii).

13. The method of claim 1 further comprising charging to the first reaction zone in (iii) at least one halogenated catalyst, comprising a phosphorus-halide bond, selected from the group consisting of $PCl_3$, $R^{17}PCl_2$, $R^{18}OPCl_2$, $[R^{19}][R^{20}]PCl$, $[R^{21}][R^{22}O]PCl$, and $[R^{23}O][R^{24}O]PCl$; wherein $R^{17}$, $R^{18}$, $R^{19}$, $R^{20}$, $R^{21}$, $R^{22}$, $R^{23}$, and $R^{24}$ are independently selected from the group consisting of $C_1$ to $C_{18}$ hydrocarbyl radicals.

14. The method of claim 13, wherein the at least one phosphorus-containing ligand in (iii) is a monodentate phosphorus-containing ligand, further comprising adjusting a second molar ratio between about 5 and about 1000, wherein the second molar ratio is defined as total moles of the halogenated catalyst charged in (iii) per million total moles of the at least one monodentate phosphorus-containing ligand charged in (iii).

15. The method of claim 1, further comprising adjusting the temperature of the reaction mixture of (iv) between about 0° C. and about 150° C.

16. The method of claim 1, further comprising pre-heating the nickel composition between 150° C. to 700° C. prior to the reducing of (ii).

17. The method of claim 1, wherein the surface area of the nickel metal is about 10 to about 50 square meters per gram of nickel metal.

18. The method of claim 1, further comprising contacting the nickel complex from the reaction mixture of (iv) with 3-pentenenitrile and hydrogen cyanide in the presence of a Lewis acid promoter in a second reaction zone to produce adiponitrile.

19. The method of claim 1, further comprising contacting the nickel complex from the reaction mixture of (iv) with 1,3-butadiene and hydrogen cyanide in a third reaction zone to produce 3-pentenenitrile, 2-methyl-3-butenenitrile, or a combination of 3-pentenenitrile and 2-methyl-3-butenenitrile.

20. The method of claim 1 further comprising contacting at least a portion of the nickel complex from the reaction mixture of (iv) with 2-methyl-3-butenenitrile in a fourth reaction zone to produce 3-pentenenitrile.

21. The method of claim 1 wherein the reducing of (ii) is performed with a reducing agent comprising carbonaceous material, hydrogen, or a combination of carbonaceous material and hydrogen at a temperature in a range of 150° C. to 700° C. and at a total pressure in a range of 0.01 atmosphere and 100 atmospheres.

22. The method of claim 1, wherein the nickel composition comprising basic nickel carbonate comprises $NiCO_3$ and $Ni(OH)_2$, wherein the basic nickel carbonate has a mass ratio of nickel to carbon of at least 10:1, the basic nickel carbonate has a molar ratio of $NiCO_3$ to $Ni(OH)_2$ of less than 1, or a combination thereof.

23. The method of claim 1, wherein the surface area of the nickel metal is about 0.5 to about 50 square meters per gram of nickel metal.

* * * * *